US007985728B1

(12) United States Patent
Murase et al.

(10) Patent No.: US 7,985,728 B1
(45) Date of Patent: Jul. 26, 2011

(54) SUSTAINED RELEASE OF APO A-I MIMETIC PEPTIDES AND METHODS OF TREATMENT

(75) Inventors: Katsuyuki Murase, Cupertino, CA (US); Li Zhao, Mountain View, CA (US); Irina Astafieva, Palo Alto, CA (US); Paul M. Consigny, San Jose, CA (US); Stephen D. Pacetti, San Jose, CA (US); Dariush Davalian, San Jose, CA (US); Syed Fayaiz Ahmed Hossainy, Fremont, CA (US); Florian N. Ludwig, Mountain View, CA (US); Jinping Wan, Mountain View, CA (US); John Stankus, Campbell, CA (US); Rachel Bright, Palo Alto, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 688 days.

(21) Appl. No.: 11/858,862

(22) Filed: Sep. 20, 2007

(51) Int. Cl.
C07K 14/00 (2006.01)
A61K 38/00 (2006.01)
(52) U.S. Cl. ............................................ 514/2; 530/300
(58) Field of Classification Search .................. None
See application file for complete search history.

(56) References Cited

U.S. PATENT DOCUMENTS

| | | | |
|---|---|---|---|
| 4,643,988 A | 2/1987 | Segrest et al. |
| 4,925,677 A | 5/1990 | Feijen |
| 5,202,745 A | 4/1993 | Sorin et al. |
| 5,291,267 A | 3/1994 | Sorin et al. |
| 5,321,501 A | 6/1994 | Swanson et al. |
| 5,365,125 A | 11/1994 | Goetting et al. |
| 5,459,570 A | 10/1995 | Swanson et al. |
| 5,465,147 A | 11/1995 | Swanson |
| 5,700,484 A | 12/1997 | Chauffard et al. |
| 5,783,600 A | 7/1998 | Bisgaier et al. |
| 5,874,075 A | 2/1999 | Collins et al. |
| 6,124,273 A | 9/2000 | Drohan et al. |
| 6,376,464 B1 | 4/2002 | Dasseux et al. |
| 6,506,799 B1 | 1/2003 | Dasseux |
| 6,602,854 B1 | 8/2003 | Dasseux et al. |
| 6,692,466 B1 | 2/2004 | Chow et al. |
| 6,753,313 B1 | 6/2004 | Dasseux et al. |
| 6,831,105 B2 | 12/2004 | Dasseux |
| 6,844,327 B2 | 1/2005 | Dasseux et al. |
| 6,852,760 B1 | 2/2005 | Fine et al. |
| 6,878,817 B2 | 4/2005 | Lees et al. |
| 6,881,860 B2 | 4/2005 | Luchoomun et al. |
| 6,900,177 B1 | 5/2005 | Dasseux et al. |
| 6,960,648 B2 | 11/2005 | Bonny |
| 7,273,469 B1 | 9/2007 | Chan et al. |
| 2004/0229794 A1 | 11/2004 | Ryan et al. |
| 2004/0254120 A1 | 12/2004 | Fogelman et al. |
| 2004/0266671 A1 | 12/2004 | Fogelman et al. |
| 2005/0118226 A1 | 6/2005 | Kovacs et al. |
| 2005/0175666 A1 | 8/2005 | Ding |
| 2005/0176623 A1 | 8/2005 | Wagle |
| 2005/0202532 A1 | 9/2005 | Bielicki et al. |
| 2005/0222029 A1 | 10/2005 | Bartel et al. |
| 2005/0232981 A1 | 10/2005 | Ben-Sasson |
| 2009/0081293 A1 | 3/2009 | Katsuyuki et al. |
| 2009/0081299 A1 | 3/2009 | Hossainy et al. |

FOREIGN PATENT DOCUMENTS

| | | |
|---|---|---|
| WO | WO-9736927 | 10/1997 |
| WO | WO-9916408 | 4/1999 |
| WO | WO-03026492 A2 | 4/2003 |
| WO | WO-03096983 | 11/2003 |
| WO | WO-2005041866 A2 | 5/2005 |
| WO | WO-2006047279 | 5/2006 |
| WO | WO-2006100567 | 9/2006 |
| WO | WO-2006100567 A1 | 9/2006 |
| WO | WO-2008048387 | 4/2008 |
| WO | WO-2008048387 A2 | 4/2008 |

OTHER PUBLICATIONS

"Arisaph Reports on Promising Results Presented at AHA: Novel APO A-I Mimetic Peptide Significantly Inhibits Atherosclerosis in Preclinical Animal Study", News Release, Arisaph Pharmaceuticals, Boston, MA, (Nov. 15, 2005), 2 pages.
PCT International Search Report (dated Dec. 5, 2009), International Application No. PCT/US2008/012767, International Filing Date—Nov. 14, 2008, (Whole Document).
Ramprasad, Mysore P., et al., "Sustained-Delivery of an ApolipoproteinE-Peptidomimetic Using Multivesicular Liposomes Lowers Serum Cholesterol Levels", Journal of Controlled Release, Elsevier, Amsterdam, NL, vol. 79, No. 1-3, Feb. 19, 2002, XP004340926, ISSN: 0168-3659, (pp. 207-218).
Abbott Cardiovascular Systems, Non Final Office Action dated Jun. 1, 2009 for U.S. Appl. No. 11/946,028.
Aragane, K., et al., "ACAT inhibitor F-1394 prevents intimal hyperplasia induced by balloon injury in rabbits", Journal of Lipid Research, 42, (2001), 480-488.
Batetta, B., et al., "Role of cholesterol ester pathway in the control of cell cycle in human aortic smooth muscle cells", FASEB Journal, 17, (2003), 746-748.
Chang, T. Y., et al., "Catalysis of ACAT may be completed within the plane of membrane: a working hypothesis", Journal of Lipid Research, 42, (2001), 1933-1938.
Datta, G., et al., "Aromatic residue position on the nonpolar face of class A amphipathic helical peptides determines biological activity", Journal of Biological Chemistry, 279(24), (2004), 26509-26517.

(Continued)

Primary Examiner — Anand U Desai
(74) Attorney, Agent, or Firm — Blakely Sokoloff Taylor & Zafman LLP

(57) ABSTRACT

A method including advancing a delivery device through a lumen of a blood vessel to a particular region in the blood vessel; and introducing a composition including a sustained-release carrier and an apolipoprotein A-I (Apo A-I) synthetic mimetic peptide into a wall of the blood vessel at the particular region, wherein the peptide has a property that renders the peptide effective in reverse cholesterol transport. A composition including an apolipoprotein A-I (Apo A-I) synthetic peptide, or combination of an Apo A-I synthetic mimetic peptide and an Acyl CoA cholesterol: acyltransferase (ACAT) inhibitor in a form suitable for delivery into a blood vessel, the peptide including an amino acid sequence in an order reverse to an order of various Apo A-I mimetic peptides, or endogenous Apo A-I analogs, or a chimera of helix 1 and helix 9 of endogenous Apo A-I.

11 Claims, 8 Drawing Sheets

OTHER PUBLICATIONS

Gupta, H., et al., "Inhibition of lipopolysaccharide-induced inflammatory responses by an apolipoprotein AI mimetic peptide", Circulation Research, 97, (2005), 236-243.

Hartgerink, J. D., et al., "Peptide-amphiphile nanofibers: a versatile scaffold for the preparation of self-assembling materials", PNAS, 99(8), (Apr. 2002), 5133-5138.

Hartgerink, J. D., et al., "Self-assembly and mineralization and peptide-amphiphile nanofibers", Science, www.sciencemag.org, 294, (Nov. 2001), 1684-1688.

Li, X., et al., "Differential effects of apolipoprotein A-I-mimetic peptide on evolving and established atherosclerosis in apolipoprotein e-null mice", Circulation, Journal of the American Heart Association, 110, (2004), 1701-1705.

Linsel-Nitschke, P., et al., "HDL as a target in the treatment of atherosclerotic cardiovascular disease", Nature Reviews Drug Discovery, 4(10), (2005), 193-205, Abstract.

Natarajan, P., et al., "Identification of an apolipoprotein A-I structural element that mediates cellular cholesterol efflux and stabilizes ATP binding cassette transporter A1", Journal of Biological Chemistry (JBC), 279(23), (2004), 24044-24052.

Navab, M., et al., "Human apolipoprotein A-I and A-I mimetic peptides: potential for atherosclerosis reversal", Current Opinion in Lipidology, 15(6), (Dec. 2004), 645-649, Abstract.

Nissen, S. E., et al., "Effect of recombinant ApoA-I milano on coronary atherosclerosis in patients with acute coronary syndromes: a randomized controlled trial", JAMA, 290(17), (Nov. 2003), 2292-2300.

Panagotopulos, S. E., et al., "The role of apolipoprotein A-I helix 10 in apolipoprotein-mediated cholesterol efflux via the ATP-binding cassette transporter ABCA1", Journal of Biological Chemistry, 277(42), (2002), 39477-39484.

Rader, D. J., "High-density lipoproteins and atherosclerosis", American Journal of Cardiology, 90(8), (Oct. 2002), 62-80.

Shah, P. K., et al., "Effects of recombinant apolipoprotein A-Imilano on aortic atherosclerosis in apolipoprotein E-deficient mice", Circulation, Journal of the American Heart Association, 97, (1998), 780-785.

Shah, P. K., et al., "High-dose recombinant apolipoprotein A-I milano mobilizes tissue cholesterol and rapidly reduces plaque lipid and macrophage content in apolipoprotein E-deficient mice: potential implications for acute plaque stabilization", Circulation, Journal of the American Heart Association, 103, (2001), 3047-3050.

Vedhachalam, C., et al., "Influence of ApoA-I structure on the ABCA1-mediated efflux of cellular lipids", Journal of Biological Chemistry (JBC), 279(48), (2004), 49931-49939.

Definition of derivative and analog from cancerweb.ncl.ac.uk/cgi-bin/omd?query=derivative, (Jul. 7, 2005), 5 pages.

"Designing Customs Peptides", SIGMA Genosys, www.sigma-genosys.com/peptide_design.asp, (Dec. 16, 2004), 2 pages.

Abbott Cardiovascular Systems, Non Final Office Action dated Jun. 1, 2009 for U.S. Appl. No. 11/946,028.

Berendsen, H., "A glimpse of the holy grail?", Science, vol. 282, www.sciencemag.org, (Oct. 1998), 642-643.

Bradley, et al., "Limits of cooperativity in a structurally modular protein: response of the notch ankyrin domain to analogous alanine substitutions in each repeat", J. Mol. Biol., 324, (2002), 373-386.

Ngo, J. T., et al., "Computational complexity, protein structure prediction, and the levinthal paradox", The Protein Folding Problem and Tertiary Structure Prediction, Birkhauser Boston, (1994), 491-495.

Rudinger, J., "Characteristics of the amino acides as components of a peptide hormone sequence", Peptide Hormones, JA, Parsons Edition, University Park Press, (Jun. 1976), 1-7.

Schinzel, R., et al., The phosphate recognition site of *Escherichia coli* maltodextrin phosphorylase, Federation of European Biochemical Societies, vol. 286, No. 1,2, (Jul. 1991), 125-128.

Voet, D., et al., "Abnormal Hemoglobins", Biochemistry, Second Edition, Section 9-3, (1995), 235-241.

Abbott Cardiovascular Systems, International search report and written opinion dated May 15, 2009 for PCT/US2008/012793.

Luck, et al., "Plasma protein adsorption on biodegradable microspheres consisting of poly(d,l-lactide-co-glycolide), poly(l-lactide) or ABA triblock copolymers containing poly(oxyethylene)—Influence of production method and polymer composition", Journal of Controlled Release, Elsevier, vol. 55, No. 2-3, (Nov. 13, 1998), 107-120.

Prokop, et al., "Nanovehicular intracellular delivery systems", Journal of Pharmaceutical Sciences, vol. 97, No. 9, (Sep. 2008), 3518-3590.

"Apo A-1 from Human", NCBI Accession No. P02647; Accessed Jun. 15, 2010, 1-14.

Abbott Cardiovascular Systems, Non final office action dated Apr. 6, 2010 for U.S. Appl. No. 11/858,851.

Abbott Cardiovascular Systems, Final Office Action dated Jun. 17, 2010 for U.S. Appl. No. 11/946,028.

Abbott Cardiovascular Systems, International Preliminary Report on Patentability mailed Jun. 10, 2010 for PCT/US2008/012793.

Abbott Cardiovascular Systems, International Preliminary Report on Patentability mailed Jun. 10, 2010 for PCT/US2008/012794.

Abbott Cardiovascular Systems, International Preliminary Report on Patentability mailed Jun. 10, 2010 for PCT/US2008/012767.

Gu, et al., "Apolipoprotein A-1 from Beijing Duck", NCBI Accession No. AAB30359; Accessed Jun. 15, 2010, 1 page.

Knott, et al., "Apolipoprotein from human", NCBI Accession No. CAA28583.1; Accessed Jun. 15, 2010, 1 page.

Ng, Pauline C., et al., "Predicting the effects of amino acid substitutions on protein function", Annu. Rev. Genom. Human Genet., vol. 7, (2006), 61-80.

Abbott Cardiovascular Systems, Non-final Office Action mailed Nov. 24, 2010 for U.S. Appl. No. 11/946,029.

Abbott Cardiovascular Systems, Non final office action mailed Oct. 19, 2010 for U.S. Appl. No. 11/946,026.

Abbott Cardiovascular Systems, Final office action mailed Sep. 17, 2010 for U.S. Appl. No. 11/858,851.

SUSTAINED RELEASE OF APO A-I MIMETIC PEPTIDES AND METHODS OF TREATMENT

SEQUENCE LISTING

A paper copy of the Sequence Listing entitled "56188863" is herein incorporated by reference. This Sequence Listing consists of SEQ. ID NOs:1-12.

FIELD OF THE INVENTION

Compositions and methods for facilitating reverse cholesterol transport.

BACKGROUND OF THE INVENTION

Cholesterol is a major component of atherosclerotic plaque. Cholesterol accumulation within atherosclerotic plaque occurs when cholesterol influx into an arterial wall exceeds cholesterol efflux. Increased influx of cholesterol into the arterial wall is accompanied by an increased influx of monocytes/macrophages, which absorb oxidized aggregated low density lipoproteins (LDL) and store the cholesterol esters.

Current strategies to reduce coronary heart disease are primarily directed at reducing the influx of cholesterol into the arterial wall by lowering LDL cholesterol concentration. While lowering of plasma LDL levels offers some protection from coronary heart disease, the protection is not complete. As a result, there is an interest in strategies aimed at enhancing cholesterol efflux from the arterial wall and promoting its transport to the liver for excretion.

Cholesterol circulating in the blood is carried by plasma lipoproteins. Plasma lipoproteins are classified into groups according to size. Of these, the low density lipoprotein (LDL) and high density lipoprotein (HDL) are primarily the major cholesterol carrier proteins. The protein component of LDL, apolipoprotein B (Apo B), constitutes the atherogenic component. Apo B is not present in HDL. HDL includes apolipoprotein A-I (Apo A-I) and apolipoprotein A-II (Apo A-II) as well as other apolipoproteins.

Various forms of HDL have been described on the basis of electrophoretic mobility and include two major fractions: a first fraction with α-HDL mobility and another fraction Various forms of HDL have been described on the basis of electrophoretic mobility and include two major fractions: a first fraction with α-HDL mobility and another fraction referred to as pre-β HDL. Pre-β HDL is thought to be the most efficient HDL subclass for inducing cellular cholesterol efflux. Pre-β HDL fractions includes Apo A-I, phospholipids and free cholesterol. Pre-β HDL are considered to be acceptors of cellular free cholesterol and are believed to transfer free and esterified cholesterol to α-HDL.

Two pathways have been proposed to describe the movement of cholesterol from a plasma membrane to acceptor particles such as pre-β HDL. In the "aqueous diffusion pathway," cholesterol molecules spontaneously desorb from cell membranes and are then incorporated into acceptor particles (pre-(HDL) after traversing the intervening aqueous space by diffusion. It is believed that the aqueous diffusion pathway does not require interaction with specific cell receptors.

The second model, referred to as the "microsolubilization pathway," involves the interaction of HDL (presumably an Apo A-I interaction) with a cell surface binding site. The HDL induces an intracellular signal leading to translocation of cholesterol from intracellular sites to the plasma membrane. The physiological acceptors or carriers for the translocated cholesterol are nascent HDL particles, including α-HDL and pre-β HDL.

Cholesterol that is transferred to nascent HDL particles is esterified by lecithin-cholesterol acyl transferase (LCAT) to cholesteryl esters. These esters are hydrophobic and tend to move into the core of the HDL particle. The HDL cholesteryl esters may return or be delivered to the liver and are excreted from the liver into bile, either directly or after conversion to bile cells.

It is believed that α-HDL and pre-β HDL particles, the primary acceptors or carriers for translocated cholesterol, do not occur in the same relative fractions as nascent HDL particle in the blood stream of an adult human. Thus, the carrier potential of each fraction is believed to be inversely proportional to its relative fraction of the total HDL quantity. In other words, the fraction with the highest carrier potential (pre-β HDL) occurs in the smallest overall amount in vivo.

SUMMARY OF THE INVENTION

Compositions, methods and treatments for improving reverse cholesterol transport are disclosed. In one embodiment, a method includes advancing a delivery device through a lumen of a blood vessel to a particular region in the blood vessel and introducing a composition including a synthetic Apo A-I mimetic peptide into a wall of the blood vessel (e.g., into a lesion) at the particular region. A treatment composition including a synthetic Apo A-I synthetic mimetic peptide may be used to induce regression of an existing plaque or to delay progression of an evolving atherosclerotic plaque. By introducing a composition including a synthetic Apo A-I mimetic peptide locally (e.g., into a lesion) or regionally (e.g., in or around an area immediately adjacent the legion), it is anticipated that less treatment agent will be lost in the systemic circulation, thereby allowing smaller (lower) doses to provide longer duration therapy. By combining the mimetic peptide with a carrier, a release profile of the peptide may be modified to provide, for example, a delayed, sustained, or controlled release of the peptide.

In another embodiment, a composition is disclosed. The composition includes an Apo A-I mimetic peptide and a carrier such as, but not limited to, a liposome, a polymerosome, a micelle, a particle (e.g., nanoparticle, microparticle, core-shell particles), or a microbubble. The Apo A-I mimetic peptide may be an amino acid sequence arranged in an order similar to or reverse to endogenous Apo-I peptide. Alternatively, the Apo A-I mimetic peptide may be an amino acid sequence arranged in an order similar to or reverse to an Apo-I mimetic peptide.

DETAILED DESCRIPTION OF THE INVENTION

Figure 1:
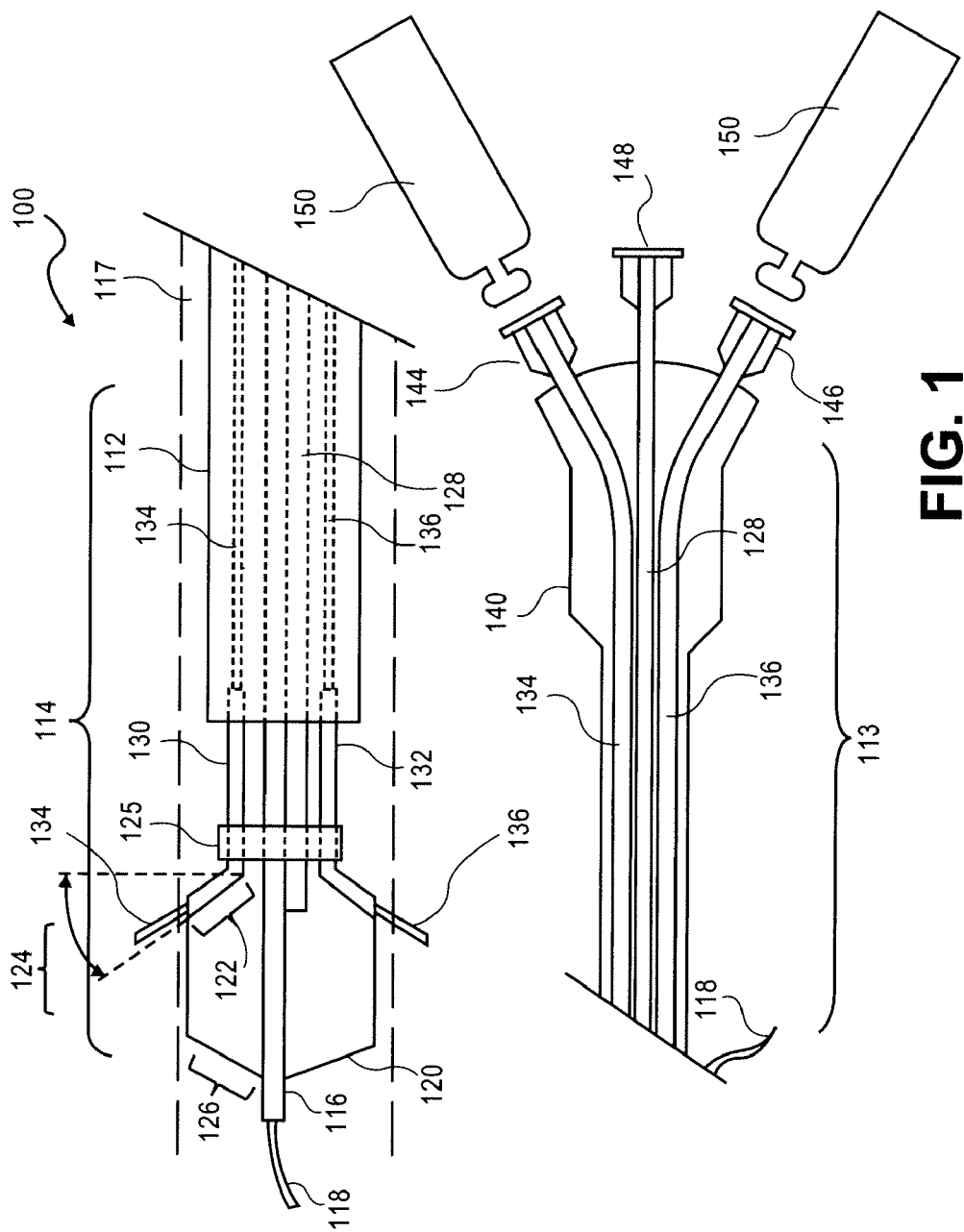
FIG. 1 is a simplified cross-sectional view of an embodiment of a substance delivery apparatus in the form of a catheter assembly having a balloon and a therapeutic substance delivery assembly.

The following embodiments describe techniques, compositions and devices directed, in one aspect, at improving reverse cholesterol transport by the aqueous diffusion pathway or the microsolubilization pathway. As noted above, direct vascular protective effects of HDL have been attributed to Apo A-I or Apo A-I-associated molecules in HDL. Amphipathic helical peptides that mimic the actions of Apo A-I have been shown to have anti-atherogenic effects in animal models.

Endogenous Apo A-I molecule (human) is a single polypeptide chain with 243 amino acids consisting of ten 22-mer amphipathic α-helices in tandem. The majority of the α-helices, i.e., helices 1, 2 and 5-8 are class A helices, while the remainder, i.e., 3-4, 9-10 are class Y helices. Endogenous Apo A-I contains a globular N-terminal domain (residues 1 to 43) and a lipid-binding C-terminal domain (residues 44 to 243). Endogenous Apo A-I is synthesized by the liver and small intestine as a preprotein (260 amino acid residues) which is secreted as a proprotein (249 amino acid residues) that is rapidly cleaved to generate a mature polypeptide having 243 amino acid residues.

Treatment Agents

In one embodiment, a synthetic Apo A-I mimetic peptide (hereinafter, referred to as a "mimetic peptide") combined with a carrier is locally delivered. "Local delivery" of a treatment composition including the mimetic peptide in this context includes delivery into a vessel wall or a lesion associated with a vessel wall such as a coronary vessel wall as opposed to delivery into the systemic circulation. Local delivery may provide enhanced delivery efficiency and minimize treatment agent (e.g., synthetic Apo A-I mimetic peptide) loss into the systemic circulation, thereby allowing application of lower doses and longer duration of activity. Local delivery also improves overall effectiveness in modulating coronary arterial response to injury.

According to some embodiments, a synthetic Apo A-I mimetic peptide "mimics" endogenous human Apo A-I in the sense that the mimetic peptide is capable of the removal of cholesterol, i.e., reverse cholesterol transport or efflux. In one embodiment, the mimetic peptide includes at least one class A amphipathic α-helix having positively charged amino acid residues clustered at a hydrophobic-hydrophilic interface and negatively-charged amino acid residues clustered at a center of a hydrophilic face. Other characteristic properties of Apo A-I mimetic peptides include peptides with a non-polar side of aromatic amino acids, like phenylalanine or tyrosine, and positively-charged amino acids (e.g., glutamic acid) between two α-helices having a suitable distance (e.g., approximately 3.6 amino acid residues).

Examples of suitable synthetic Apo A-I mimetic peptides that may be locally delivered include, but are not limited to:

(i) An 18 amino acid peptide 4F (L-4F, D-4F), DWFKAFYDKVAEKFKEAF (SEQ ID NO: 1), and its homologs, derivatives and analogs;

(ii) An 18 amino acid peptide, DWLKAFYDKVAEKLKEAF (SEQ ID NO: 2), and its homologs, derivatives and analogs; and (iii) A 33 amino acids peptide, PALEDLRQGLLPVLESFKVFLSALEEYTKKLNTQ (SEQ ID NO: 3), and its homologs, derivatives and analogs.

As described, the 18-mer and 33-mer peptides begin at the amino end of a polypeptide chain (e.g., the peptide chain is read left to right starting with the amino-terminal residue). One of ordinary skill in the art would appreciate that "D" and "L" designations refer to the enantiomers of s compound based on the actual geometry of each enantiomer.

Other amphipathic helix peptides, such as Apo A-II and Apo J peptide, and the homologs, derivatives and analogs thereof are also suitable. Peptides may consist of D amino acids, L amino acids, a racemic backbone of D and L amino acids, or any mixture thereof. The N-terminal may be modified by components including, but not limited to, acetyl groups, and C-terminal carboxyl may be modified by components, including but not limited to, amides or esters. These modified peptide structures may provide protection against premature degradation. Examples of modified peptides include, but are not limited to:

(iv) An 18-mer peptide, 4F: Ac-DWFKAFYDKVAEKFKEAF-NH$_2$ (SEQ ID NO: 4); and (v) A 33-mer peptide, helices 9/10: Ac-PALEDLRQGLLPVLESFKVFLSALEEYTKKLNTQ-NH$_2$ (SEQ ID NO: 5).

The amino acids represented by letters in the above examples and throughout this description are as follows:

| | | |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

The 18-mer D-4F peptide mimetic has been shown to be effective in reverse cholesterol transport without a lipid complex. However, this peptide may be administered in the form of a phospholipid complex as can other peptides described herein. Incompletely lipidated endogenous Apo A-I, existing as a flexible conformation or molten globular state, is known to readily associate with lipids due to its amphipathic α-helical segments. Thus, mimetic peptides according to embodiments of the invention are expected to similarly associate with lipids due to inclusion of at least one amphipathic α-helical segment. In one embodiment, a synthetic Apo A-I mimetic peptide may be formulated as a complex with a phospholipid such as dimyristoyl phosphocholine (DMPC) to form a lipid complex. Both 18-mer L-4F and D-4F mimetic peptides have been shown to function more effectively in reverse cholesterol transport in vitro when a phospholipid complex is presented. The 33-mer peptide mimetic, in particular, requires phospholipid complex formation for effective reverse cholesterol transport.

As noted above, endogenous Apo A-I molecule (human) is a single polypeptide chain with 243 amino acids consisting of 10 amphipathic α-helices. One unit of helix turns consistently and includes 3.6 amino acid residues. Therefore, even though a peptide sequence is reversed, a relative location of hydrophobic and hydrophilic side chains is similar to the original peptide when peptides form α-helix structure. Thus, in another embodiment, a suitable Apo A-I synthetic mimetic peptide for atherosclerosis treatment (e.g., reverse cholesterol transport) is a peptide including amino acids arranged in an order reverse to the order of an endogenous Apo A-I peptide or a portion thereof.

Examples of reverse sequence synthetic Apo A-I mimetic peptides (with optionally modified N- and C-terminals) include, but are not limited to:
(vi) Ac-FAEKFKEAVKDYFAKFWD-NH$_2$ (SEQ ID NO: 6) (4F);
(vii) Ac-FAEKLKEAVKDYFAKLWD-NH$_2$ (SEQ ID NO: 7); and
(viii) Ac-NLKKTYEELASLFSVKFSELVPLLGQRL-DELAP-NH$_2$ (SEQ ID NO: 8).

The reverse sequence Apo A-I peptides may be formulated as phospholipid complexes and/or prepared as a treatment composition with, for example, a buffer as described above.

Work with the secondary structure of Apo A-I has identified helix 1 as having high lipid binding affinity. The chimera of helices 1 and 9 has demonstrated high hydrophobicity and an acceptable phospholipid arrangement (e.g., DMPC clearance). Thus, in one embodiment, a suitable Apo A-I synthetic peptide mimetic for atherosclerosis therapy is a chimera of helices 1 and 9. The peptides may be represented as follows:
(ix) 1/9 chimera: Ac-LKLLDNWDSVTSTFSKLREQLG-PALEDLRQGLL-NH$_2$ (SEQ ID NO: 9); and
(x) 9/1 chimera: Ac-PALEDLRQGLLPKLLDNWDSVT-STFSKLREQLG-NH$_2$ (SEQ ID NO: 10).

In this context, a chimera is a recombinant DNA molecule containing unrelated genes in the sense that the genes are each not a component of the same α-helix of the 10 α-helices of endogenous Apo A-I.

In the embodiments of the chimera of helices 1 and 9 described above, the peptides may be modified (as shown) with an N-terminal acetyl group and a C-terminal amide or ester to stabilize the amphipathic nature of the helices. The peptides may further be formulated as phospholipid complexes with, for example, DMPC, to act as an acceptor for cholesterol and/or prepared as a treatment composition with, for example, a buffer. The peptides may be synthesized or fabricated by recombinant methods with L- or D-amino acids. Still further, the reversed sequences should have similar potency.

EXAMPLE

The mimetic peptides described here can be synthesized by both Di-tert-butyldicarbonate (Boc)-, and N-α-(9-Fluorenylmethoxycarbonyl)-N-γ-trityl-L-asparagine (Fmoc)-based solid phase synthesis. Described herein is Fmoc-based solid phase peptide synthesis. Rink amide resins, for example, Rink Amide MBHA resin, or Fmoc-PAL-PEG-PS resin are used to install carboxyamides at the C-terminus of the synthesized peptides. For peptides with unmodified C-terminus, Wang resin is used for solid phase peptide synthesis (SPSS). Any other resins for SPSS can be used to synthesize peptides according to embodiments of the invention. Upon completion of peptide synthesis, if necessary, the peptide N-terminus is modified by treatment with, for example, acetic anhydride (10 eq.) and diisopropylethylamine (DIPEA) (10 eq.), or any carboxylic acid derivatives (2-5 eq.) in N,N-dimethylformamide (DMF)/dichloromethane (DCM) (1:1, v/v) with coupling reagent (2-5 eq.) and base (2-5 eq.). Side chain protection groups were removed and the peptide is simultaneously cleaved from the resin with cleavage cocktails, such as Reagent K, or 94% trifluoroacetic acid (TFA), 2.5% water, 2.5% ethanedithiol (EDT), and 1% triisopropylsilane (TIS) for cysteine-containing peptide, or any other appropriate cleavage cocktails. Purification of peptides was performed by preparative high performance liquid chromatography (HPLC) or liquid chromatography/mass spectrometry (LC/MS) with a water/acetonitrile gradient containing 0.1% TFA or formic acid. When necessary, counter ion can be exchanged to another acid, such as acetic acid. For amino acid coupling, the following coupling reagent can be used (but other reagents can also be used for peptide synthesis): N,N'-dicyclohexyl-carbodiimide (DCC), benzotriazole-1-yl-oxy-tris-(dimethylamino)-phosphonium hexafluorophosphate (BOP), benzotriazole-1-yl-oxy-tris-pyrrolidino-phosphonium hexafluorophosphate (PyBOP), (1H-Benzotriazol-1-yl)1,1,3,3-tetramethyluronium hexafluorophosphate (HBTU), 1H-Benzotriazolium-1-[bis(dimethylamino)methylene]tetrafluoroborate-(1,3)-oxide (TBTU), 2-(5-norbornene-2,3-dicarboximido)-1,1,3,3-tetramethyluronium tetrafluoroborate (TNTU), O—(N-succinimidyl)-N,N,N',N'-tetramethyluronium tetrafluoroborate (TSTU), and bromo-tris-pyrrolidino phosphoniumhexafluorophosphate (PyBrOP). 1-Hydroxybenzotriazole anhydrous (HOBt) can be added to the reaction mixture to prevent side reaction and act as catalyst.

Carriers

According to embodiments of the invention, a delivery composition including a synthetic Apo A-I mimetic peptide also includes a carrier. In one embodiment, the Apo A-I mimetic peptide can be encapsulated, suspended, disposed within or on (chemisorbed), or loaded into a biodegradable carrier. One of ordinary skill in the art would know that the amount of mimetic peptide is given in various dosages, including maximum and minimum amounts. Examples of biodegradable carriers include, but are not limited to, a liposome, a polymerosome, a micelle, a particle, a microbubble, and a gel. Examples of particles include, but are not limited to, microparticles, nanoparticles, and core-shell particles. In some embodiments, the biodegradable carrier is formulated such that it is bioerodable when present in physiological conditions.

In one embodiment, the biodegradable carrier for a synthetic Apo A-I mimetic peptide is a liposome. "Liposomes" are artificial vesicles that are approximately spherical in shape and can be produced from natural phospholipids, sphingolipids, ceramides, cholesterol or estradiol. Generally, a liposome has a lipid bilayer membrane encapsulating an aqueous solution, i.e., "core." The lipid bilayer membrane allows for fusion with an endogenous (or exogenous) cell membrane, which, similar to the liposome, comprises a semipermeable lipid bilayer. In one example, the peptide mimetic may be included in the lipid bilayer of the liposome (as opposed to within the core). This can be achieved either during liposome formation or in a post-insertion method. It is anticipated that such an embodiment will provide simultaneous extraction of cholesterol from a vulnerable plaque lesion and a potential for alteration of liposomal structure rigidity resulting in altered mass transport properties.

In one method, phospholipids and synthetic Apo A-I mimetic peptide are mixed with estradiol in chloroform. Suitable phospholipids include, but are not limited to, dimyristoylphosphatidylcholine (DMPC), dipalmitoyl phosphatidyl ethanolamine (DPPE), 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1,2-dioleoyl-sn-glycero-3-phosphocholine (DOPC), 1-dalmitoyl-2-oleoyl-sn-glycero-3-phosphocholine (POPC), Egg phosphatidylcholine (EPC), hydrogenated egg phosphatidylcholine (1-IEPC), soybean phosphatidylcholine (SPC), hydrogenated soybean phosphatidylcholine (HSPC). The liposomes may also be hydrophilically modified by coating with an agent such as poly(ethylene glycol) or dextran. Such coating tends to avoid detection from the body's immune system. After mixing, the solvent (and optional co-solvent) can be evaporated with heat or ambient temperature in a round bottom flask. Resultant lipids will be deposited on the glass surface. The deposited lipid film will be re-suspended in aqueous solution to form multilamellar (or unilamellar) vesicles, and extruded to prepare appropriate sized liposomes. Liposomes can be in a range from about 25 nm to about 2000 nm.

In another embodiment, the biodegradable carrier for a synthetic Apo A-I mimetic peptide is a polymerosome. "Polymerosomes" are polymer vesicles formed from di-block or tri-block copolymers with blocks of differing solubility. Polymerosomes may be formed by methods such as film rehydration, electro-formation and double emulsion. In some methods, a similar manufacturing technique can be used as that of a liposome to form polymerosomes. For example, a polymerosome can be a di-block copolymer including a block which is hydrophobic, e.g., poly lactic acid, polycaprolactone, n-butyl acrylate, and another block which is hydrophilic, e.g., poly (ethylene glycol), poly(acrylic acid). A polymerosome can be in a range from between about 25 nm to about 2000 nm.

In another embodiment, the biodegradable carrier for a synthetic Apo A-I mimetic peptide is a micelle. A "micelle" is an aggregate of surfactant or polymer molecules dispersed in a liquid colloid. Micelles are often globular in shape, but other shapes are possible, including ellipsoids, cylinders, bilayers, and vesicles. The shape of a micelle is controlled largely by the molecular geometry of its surfactant or polymer molecules, but micelle shape also depends on conditions such as temperature or pH, and the type and concentration of any added salt.

Micelles can be formed from individual block copolymer molecules, each of which contains a hydrophobic block and a hydrophilic block. The amphiphilic nature of the block copolymers enables them to self-assemble to form nanosized aggregates of various morphologies in aqueous solution such that the hydrophobic blocks form the core of the micelle, which is surrounded by the hydrophilic blocks, which form the outer shell. The inner core of the micelle creates a hydrophobic microenvironment for mimetic peptide, while the hydrophilic shell provides a stabilizing interface between the micelle core and an aqueous medium. Examples of polymers which can be used to form micelles include, but are not limited to, polycaprolactone polyethylene oxide blocks, polyethylene oxide-β-polypropylene oxide-β-polyethylene oxide triblock copolymer and copolymers which have a polypeptide or polylactic acid core-forming block and a polyethylene oxide block. A micelle can be in a range from between about 10 nm to about 100 nm.

In another embodiment, the biodegradable carrier for a synthetic Apo A-I mimetic peptide is a nano or micro-particle. Various methods can be employed to formulate and infuse or load the particles with a mimetic peptide. Representative methods include, but are not limited to, water/oil/water emulsion, electrohydrodynamic atomization, and electrospraying. In one example, the particles are prepared by a water/oil/water ($W_1/O/W_2$) double emulsion method. In the $W_1$ phase, an first aqueous phase is dispersed into the oil phase consisting of polymer (or other platform) dissolved in organic solvent (e.g., dichloromethane) and the synthetic Apo A-I mimetic peptide (according to embodiments of the invention) using a high-speed homogenizer. Examples of polymers include, but are not limited to, poly(L-lactide-co-glycolide) (PLGA), poly(D,L-lactide-co-glycolide), poly(L-lactide), poly(D,L-lactide) (PLA), poly(ε-caprolactone), poly(L-lactide-co-caprolactone), poly(D,L-lactide-co-caprolactone), cross-linked poly(ethylene glycol) (PEG), PLA-PEG co-polymers, poly-ester-amide co-polymers (PEA), and polyphosphazines. Additionally, collagen, gelatin, fibrin, or alginate may be used as a platform. The primary water-in-oil (W/O) emulsion is then dispersed in a second aqueous solution containing a polymeric surfactant, e.g., poly(vinyl alcohol) (PVA) or PEG, and further homogenized to produce a W/O/W emulsion. After stirring for several hours, the particles are collected by filtration. A microparticle can be in a range from about 5 μm to about 200 μm, preferably 10 μm to 50 μm. A nanoparticle can be in a range from between about 10 nm to about 500 nm, preferably about 50 nm to about 300 nm.

In an embodiment in which PEG is used (as a platform or surfactant), it is anticipated that PEG will migrate to the surface of the particle to prevent premature release of the synthetic Apo A-I mimetic peptide during therapeutic application, thus achieving sustained-release of the mimetic peptide. In another embodiment, the surface of the particle can be modified with a cardiovascular targeting molecule to achieve targeting and sustained-release of the mimetic peptide. Such targeting molecules can also be covalently bound to the polymer or other platform, or even to the mimetic peptide itself. An example of a cardiovascular targeting molecule is CRPPR (SEQ ID NO: 11) peptide. In yet another embodiment, a hydrophobic sacrificial layer can be coated onto the particle to mitigate premature peptide release. An example of a material which may be used for the sacrificial layer is a polyanhydride layer made of CPPP (SEQ ID NO: 12), or, alternatively, bioabsorbable iron- or phosphorous-doped glass or ceramic. It is anticipated that a sacrificial layer-coated particle having the mimetic peptide will be suitable for oral delivery since such a coating should be able to withstand the environment of the gastrointestinal tract.

In another embodiment, the biodegradable carrier for a synthetic Apo A-I mimetic peptide is a core-shell particle. Core-shell particles can be formed using various techniques such as, for example, electrospraying. In one exemplary method of fabricating core-shell particles, a first liquid solution ($L_1$) may be supplied to an outer tube by a pump and a second different liquid solution ($L_2$) may be supplied to an inner tube by a pump to form the core-shell particles. Solution $L_1$ may be the precursor solution that forms the (hydrophobic or hydrophilic) "shell" while solution $L_2$ may be the precursor solution that forms the (hydrophilic or hydrophobic) "core" of the particles that will be eventually collected on a collection target as the electrospray system is being operated. By creating core-shell particles encapsulating the mimetic peptide, different release profiles may be obtained as the core and shell independently (or not independently) erode after delivery to a treatment site over a period of time (condition dependent).

In another embodiment, the carrier is a nanofiber or nanorod (hereinafter referred to interchangeably) formed from self-assembled peptides. Nanorods can be formed by methods known by those skilled in the art, such as those described in J. D. Hartgerink, et al., *Self-Assembly and Mineralization of Peptide Amphiphile Nanofibers*. Science, 294 (2001): 1685-1688; J. D. Hartgerink, et al., *Peptide-Amphiphile Nanofibers: A versatile scaffold for the preparation of self-assembling materials*. PNAS, 99 (2002): 5133-5138.

In a further embodiment, the carrier is a gel. A "gel" is an apparently solid, jelly-like material formed from a colloidal solution. By weight, gels are mostly liquid, yet they behave like solids. Representatively, the gel is a solution of degradable polymers. For example, the gel can be an inversion gel of a biodegradable polymer in organic media. An example is PLA dissolved in benzyl benzoate containing the mimetic peptide. In some embodiments, the gel is a biodegradable, viscous gel. For example, the gel can be a solution of sucrose acetate isobutyrate in ethanol/water combined with the mimetic peptide. In an example where the gel includes a water-miscible organic solvent plus a polymer, a process of phase inversion occurs when the gel is introduced into the body. As the solvent diffuses out, and the water diffuses in, the polymer phase inverts, or precipitates, forming a depot of varying porosity and morphology depending on the composition. Gels can also consist of water soluble polymers in an aqueous carrier. These can provide a faster release of a peptide (e.g., a mimetic peptide), drug or other agent.

In a still further embodiment, the carrier to be used with a synthetic Apo A-I mimetic peptide is a lipid-coated microbubble (LCM) including the peptide. Peptides can be incorporated into the microbubbles in a number of different ways, including binding of a peptide to the microbubble shell and attachment of site-specific ligands. Perfluorocarbon-filled albumin microbubbles avidly bind proteins and synthetic peptides and are sufficiently stable for circulating in the vasculature as blood pool agents. These microbubbles act as carriers of these agents until a site of interest is reached. Ultrasound applied over the skin surface can then be used to burst the microbubbles at a treatment site, causing localized release of the peptide or protein. Albumin-encapsulated microbubbles have also demonstrated a property to adhere to a vessel wall. These microbubbles provide targeted delivery without the application of ultrasound. Microbubbles have also been shown to directly take up genetic material, such as plasmids and adenovirus, and phospholipid-coated microbubbles have a high affinity for certain drugs.

The mechanisms by which ultrasound facilitates the delivery of drugs and genes result from an interplay among the therapeutic agent, the microbubble characteristics, the target tissue, and the nature of ultrasound energy. The presence of microbubbles in the insonified field reduces the peak negative pressure needed to enhance delivery with ultrasound. This occurs because the microbubbles act as nuclei for cavitation, decreasing the threshold of ultrasound energy necessary to cause this phenomenon. The results of optical and acoustical studies have suggested the following mechanisms for microbubble destruction by ultrasound: gradual diffusion of gas at low acoustic power; formation of a shell defect with diffusion of gas; immediate expulsion of the microbubble shell at high acoustic power; and dispersion of the microbubble into several smaller bubbles.

In an alternative embodiment, the spatially distinct hydrophobic and charged domains of a synthetic Apo A-I mimetic peptide may hold a bioactive typically used in cardiovascular treatment. In that sense, the mimetic peptide itself acts as the "carrier." Examples of bioactives include, but are not limited to, statins such as atorvastatin, cerivastatin, fluvastatin, lovastatin, mevastatin, pitavastatin, pravastatin, rosuvastatin, and simvastatin; nitroglycerin; Acyl CoA cholesterol: acyltransferase (ACAT) inhibitor; anti-inflammatory steroids such as corticosteroids; singlet oxygen generators such as porphyrins and sub-classes thereof, such as texaphyrins, sapphyrins, pentaphyrins, porphycenes and porphyrin vinylogues in addition to tin ethyl etiopurpurin (PURLYTIN), rostaporfin (PHOTREX), verteporfin (VISUDYNE), and TEXAPRIM; phthalocyanines; immunosuppressant or anti-cancer agents such as paclitaxel, sirolimus, everolimus, ABT-578, and eptoposide.

Combination Therapies

Acyl CoA Cholesterol: Acyltransferase Inhibitors

Apo A-I or Apo A-I-related molecules (e.g., peptides) have been shown to remove cholesterol from atherosclerotic lesions through reverse cholesterol transport. In general, Apo A-I has the ability to remove free cholesterol from cell membranes, however, esterified cholesterol mainly located in lipid droplets may not be directly removed by reverse cholesterol transport.

Acyl CoA cholesterol: acyltransferase (ACAT) is an enzyme that converts free cholesterol into cholesterol esters, and is responsible for the deposition of cholesterol in cells as cholesterol esters. Inhibition of the enzyme can increase the amount of free cholesterol that can be removed by Apo A-I. In addition, oral administration of an ACAT inhibitor in rabbits prevents intimal hyperplasia induced by balloon injury through prevention of foam cell accumulation, and the effect appears independent of plasma cholesterol concentration.

ACAT is a membrane protein and the active center is located inside of the membrane. Thus, most ACAT inhibitors are highly hydrophobic and are therefore inadequate for oral administrations.

In accordance with other embodiments of the invention, a method of local or regional delivery of an ACAT inhibitor is described. The ACAT inhibitor may be delivered as a single treatment agent or in combination with Apo A-I therapy as described in embodiments of the invention. Local administration of ACAT inhibitors to the blood vessels in combination with mimetic peptides according to embodiments of the invention can maximize reverse cholesterol transport (e.g., reverse cholesterol efflux). This may improve the suppression of lipid accumulation in macrophage, of macrophage activity, and of smooth muscle cell proliferation. In addition, potential over-production of free cholesterol by inhibition of ACAT, which could cause cell damage, may be minimized by the treatment with mimetic peptides according to embodiments of the invention.

The amount of ACAT inhibitors in regional therapy formulations would be small and systemic exposure of the ACAT inhibitors would be negligible, thus, inherent side effects of ACAT inhibitors, such as liver and adrenal toxicity can be circumvented. Examples of ACAT inhibitors are listed as follows, but other ACAT inhibitors may be used as well: CP 113,818 (Pfizer), C1-1011 (Pfizer), (Avasimibe), CI-976, CL-277,082, Eflucimibe (bioMrieux-Pierre Fabre/Eli Lilly), CS-505 (Sankyo Pharma/Kyoto Pharma), (Pactimibe), KY-455 (Kyoto Pharma), F-1394 (Fujirebio Inc.), F 12511, NTE-122 (Nissin Food Products Co., Ltd.), PD 140296 (Parke-Davis), PD 128042 (Parke-Davis), PD 132301-2 (Parke-Davis), (Octimibate), DuP 128, DuP 129, 58-035 (Sandoz), HL-004, SMP-500 (Sumitomo Pharma), SMP-797, SM-32504 (Sumitomo Pharma), SKF-99085 (Glaxo Smith-Kline), E5324, R-755 (Nihon Nohyaku), FR145237 (Fujisawa Pharmaceutical Co., Ltd.), FR129169 (Fujisawa Pharmaceutical Co., Ltd.), FR186054, YM-17E (Yamanouchi Pharma), YM750 (Yamanouchi Pharma), Tamoxifen, MCC-147, YIC-708-424 (Yakult), TS-962 (Taisho), K-604 (Kowa), FCE-28654A (Pharmacia & Upjohn Inc.), CEB-925 (Wyeth).

In one embodiment, an Apo A-I synthetic peptide is part of a delivery composition. In addition to the peptide, the composition may include a phospholipid such as DMPC and a buffer such as phosphate buffered saline (PBS) that may serve to maintain an osmotic pressure and control the pH of the delivery composition. As noted above, the phospholipid component is optional, particularly with peptides that have demonstrated an ability to function in a non-complex form, such as the 18-mer L4-F and D4-F.

Other

In some embodiments, if the bioactive is a hydrophobic molecule, the bioactive may facilitate self-assembly of the mimetic peptide by serving as a nidus for self-assembly. Examples of hydrophobic molecules include, but are not limited to, hydrophobic pro-drugs such as lipid-conjugated small molecule agents. In one embodiment, a hydrophobic vasodilatory agent such as isosorbide-5-mononitrate can be conjugated through its hydroxyl group to a fatty acid to form a pro-drug ester that can slowly be released upon hydrolysis of the ester bond.

In some embodiments, it is anticipated that a synergistic effect can be achieved by combination delivery or co-delivery of a peptide mimetic and another agent. For example, a peptide mimetic may be delivered (simultaneously or subsequently) with cholesterol esterase. The cholesterol esterase converts esterified cholesterol to free cholesterol thereby facilitating reverse cholesterol transport by the mimetic peptide. In another example, a peptide mimetic may be delivered (simultaneously or subsequently) with a nitric oxide-releasing agent such as PEA-TEMPO or poly(L-arginine).

Delivery Methods

In one embodiment, a method includes advancing a delivery device through a lumen of a blood vessel to a particular region in a blood vessel such as a lesion area in a coronary atherosclerotic region. A composition including a carrier and an Apo A-I synthetic peptide is then introduced into a wall of the blood vessel at the lesion area. By introducing the Apo A-I synthetic peptide into the lesion area, significantly less peptide may be used relative to the amount that might be used in a systemic delivery treatment regimen. In one embodiment, an amount target of a five microgram Apo A-I peptide/kilogram (μg/kg) for an adult human is suitable. The delivery device may also be used to introduce an ACAT inhibitor(s), possibly in similar amounts, into or beyond the blood vessel at or adjacent the lesion area.

Referring now to the drawings, FIG. 1 illustrates one embodiment of a delivery apparatus. In general, the delivery apparatus provides a system for delivering an Apo A-I synthetic peptide or a treatment composition including an Apo A-I synthetic peptide, to or through a desired area of a blood vessel (a physiological lumen) or tissue in order to treat a localized area of the blood vessel. The delivery apparatus is similar in certain respects to the delivery apparatus described in commonly-owned, U.S. patent application Ser. No. 09/746,498 (filed Dec. 21, 2000), titled "Local Drug Delivery Catheter with Retractable Needle," of Chow et al. (issued as U.S. Pat. No. 6,692,466) and U.S. patent application Ser. No. 10/749,354 (filed Dec. 31, 2003), titled "Modified Needle Catheter for Directional Orientation Delivery" of Chan, et al. Each of these applications is incorporated herein by reference. The delivery apparatus described is suitable, in one embodiment, for a percutaneous delivery of a treatment agent where a desired form of the treatment agent is introduced through a single catheter needle.

Referring to FIG. 1, the delivery apparatus includes catheter assembly 100, which is intended to broadly include any medical device designed for insertion into a blood vessel or physiological lumen to permit injection and/or withdrawal of fluids, to maintain the patency of the lumen, or for any other purpose. In one embodiment, catheter assembly 100 is defined by elongated catheter body (cannula) 112 having proximal portion 113 and distal portion 114. In one embodiment, proximal portion 113 may reside outside a patient during a procedure while distal portion 114 is placed at a treatment site, for example, within coronary blood vessel 117.

Catheter assembly 100 includes catheter body 112 having a lumen therethrough extending from proximal portion 113 to distal portion 114. In this example, guidewire cannula 116 is formed within catheter body 112 for allowing catheter assembly 100 to be fed and maneuvered over a guidewire (guidewire 118 shown at this point within a lumen of guidewire cannula 116). Guidewire cannula 116 may extend from proximal portion 113 to distal portion 114, thus describing an over the wire (OTW) assembly. In another embodiment, typically described as a rapid exchange (RX) type catheter assembly, guidewire cannula 116 extends only through a portion of catheter body 112, for example, beginning and ending within distal portion 114. An RX type catheter assembly is shown. It is appreciated that guidewire 118 may be retracted or removed once catheter assembly 100 is placed at a region of interest, for example, within a blood vessel (e.g., artery or vein).

In the embodiment of FIG. 1, catheter assembly 100 includes balloon 120 incorporated at distal portion 114 of catheter assembly 100. Balloon 120 is an expandable body in fluid communication with inflation cannula 128 disposed within catheter body 112. Inflation cannula 128 extends from balloon 120 within distal portion 114 through inflation port 148 at proximal portion 113 (e.g., at a proximal end of catheter assembly 100). Inflation cannula 128 is used to deliver a fluid to inflate balloon 120.

In the embodiment shown in FIG. 1, balloon 120 is in an expanded or inflated state that occludes blood vessel 117. Balloon 120 is selectively inflatable to dilate from a collapsed configuration to a desired or controlled expanded configuration. Balloon 120 can be selectively inflated by supplying a fluid (e.g., liquid) into a lumen of inflation cannula 128 at a predetermined rate of pressure through inflation port 148. Likewise, balloon 120 is selectively deflatable to return to a collapsed configuration or deflated profile.

In one embodiment, balloon 120 can be defined by three portions: distal taper wall 126, medial working length 124, and proximal taper wall 122. In one embodiment, proximal taper wall 122 can taper at any suitable angle θ, typically between about 15° to less than about 90°, when balloon 120 is in an expanded (inflated) configuration.

Balloon 120 can be made from any suitable material, including, but not limited to, polymers and copolymers of polyolefins, polyamides, polyester and the like. The specific material employed should be compatible with inflation or expansion fluid and must be able to tolerate the pressures that are developed within balloon 120. One suitable material is an elastomeric nylon such as PEBAX™, a condensation polymerized polyether block polyamide. PEBAX™ is a trademark of ATOCHEM Corporation of Puteaux, France. Other suitable materials for balloon 120 include, but are not limited to, a biocompatible blend of polyurethane and silicone, or a styrenic block copolymer (SBC) or blend of SBCs. Distal taper wall 126, medial working length 124, and proximal taper wall 122 can be bound together by seams or be made out of a single seamless material. A wall of balloon 120 (e.g., at any of distal taper wall 126, medial working length 124 and/or proximal taper wall 122) can have any suitable thickness so long as the thickness does not compromise properties that are critical for achieving optimum performance. Relevant properties include, but are not limited to, high burst strength, low compliance, good flexibility, high resistance to fatigue, the ability to fold, the ability to cross and recross a desired region of interest or an occluded region in a physiological lumen and low susceptibility to defects caused by handling. By way of example, not limitation, a suitable thickness of a balloon wall can be in the range of about 0.0005 inches to 0.002 inches, the specific specifications depending on the procedure for which balloon 120 is to be used and the anatomy and size of the target lumen in which balloon 120 is to be inserted.

Balloon 120 may be inflated by the introduction of a fluid (e.g., liquid) into inflation cannula 128 (through inflation port 148 at a point outside a physiological lumen). Liquids containing therapeutic and/or diagnostic agents may be used to inflate balloon 120. In one embodiment, balloon 120 may be made of a material that is permeable to such therapeutic and/or diagnostic agents thus providing a method of delivering a therapeutic and/or diagnostic agent at a treatment site in addition to an Apo A-I peptide, a treatment composition including an Apo A-I peptide or an ACAT inhibitor. To inflate balloon 120, a suitable fluid may be supplied into inflation cannula 128 at a predetermined pressure, for example, between about one and 20 atmospheres (atm). A specific pressure depends on various factors, such as the thickness of the balloon wall, the material of which balloon 120 is made, the type of substance employed, and the flow rate that is desired.

Catheter assembly 100, in the embodiment shown in FIG. 1 also includes delivery cannula 130 and delivery cannula 132 each connected to proximal taper wall 122 of balloon 120 and extending at a proximal end, in one embodiment, into a portion of catheter body 112 of catheter assembly 100. Representatively, a suitable length for delivery cannula 130 and delivery cannula 132 is on the order of three to 6.5 centimeters (cm). Delivery cannula 130 and delivery cannula 132 can be made from any suitable material, such as polymers and copolymers of polyamides, polyolefins, polyurethanes, and the like. Catheter assembly 100, in this view, also includes needle 134 and needle 136. Needle 134 and needle 136 extend from distal portion 114 to proximal portion 113 of catheter assembly 100. At distal portion 114, needle 134 is slidably disposed through a lumen of delivery cannula 130 and needle 136 is slidably disposed through a lumen of delivery cannula 132. Thus, a dimension of delivery cannula 130 and delivery cannula 132 are each selected to be such to allow a delivery device such as a needle to be moved therethrough. Representatively, delivery cannula 130 has an inner diameter (lumen diameter) on the order of 0.002 inches to 0.020 inches (e.g., 0.0155 inches) and an outer diameter on the order of 0.006 inches to 0.05 inches (e.g., 0.0255 inches). FIG. 1 shows catheter assembly 100 with each of needle 134 and needle 136 deployed in an extended configuration, i.e., extending from an end of delivery cannula 130 and delivery cannula 132, respectively. In a retracted configuration, the needles retract proximally into the delivery cannula lumens. Although two needles are shown, in another embodiment, catheter assembly may include only a single needle (and single delivery cannula) or may include more than two needles (and more than two delivery cannulas).

FIG. 1 shows delivery cannula 130 and delivery cannula 132 each connected to an exterior surface of balloon 120. Specifically, a distal end of each of delivery cannula 130 and delivery cannula 132 extend to a point equivalent to or less than a length of proximal taper wall 122 of balloon 120. One suitable technique for connecting delivery cannula 130 or delivery cannula 132 to balloon 120 is through an adhesive. A suitable adhesive includes a cyanoacrylate (e.g., LOCTITE 414™) adhesive, particularly where the balloon material is a PEBAX™ material.

Catheter assembly 100 in the embodiment shown in FIG. 1 also includes sheath ring 125. Sheath ring 125 is positioned over, in this embodiment, guidewire cannula 116, inflation cannula 128, delivery cannula 130, and delivery cannula 132, respectively. In one embodiment, sheath ring 125 functions to inhibit delamination of the delivery cannulas from proximal taper wall 122 of balloon 120 and, where thermally sealed to the various cannulas may reduce the spacing (on a proximal side of sheath ring 125) of the cannulas. Thus, a distal end of sheath ring 125 is placed, in one embodiment, at a point immediately proximal to where a delivery cannula will rotate, bend or plicate in response to the expansion or inflation of balloon 120. In one embodiment, sheath ring 125 is a biocompatible material that is capable of connecting to (e.g., bonding to) a material for balloon 120 and to a material for each of the noted cannulas that it surrounds. Representatively, a body of sheath ring 125 has a length from a proximal end to a distal end on the order of 0.25 millimeters (mm) to 0.75 mm, such as 0.5 mm.

As noted above, each delivery cannula (e.g., delivery cannula 130, delivery cannula 132) plicates or bends distal to sheath ring 125 with the inflation of balloon 120. Thus, the path to be traveled by each needle (e.g., needle 134 and needle 136) includes this bend or plication. To facilitate a travel through a bend or plication region in each delivery cannula and to inhibit puncturing of the respective delivery cannula, each delivery cannula may include a deflector disposed along an interior wall. Representatively, a suitable deflector includes a ribbon of thin, generally flexible and generally resilient material (e.g., thickness on the order of about 0.0005 inches to about 0.003 inches and width on the order of about 0.005 inches and 0.015 inches). Suitable deflector materials, dimensions and connections within a catheter assembly are described in commonly-owned, U.S. patent application Ser. No. 09/746,498 (filed Dec. 21, 2000), titled "Local Drug Delivery Catheter with Retractable Needle," of Chow et al. (issued as U.S. Pat. No. 6,692,466) and U.S. patent application Ser. No. 10/749,354 (filed Dec. 31, 2003), titled "Modified Needle Catheter for Directional Orientation Delivery." of Chan, et al.

Referring again to FIG. 1, proximal portion 113 of catheter assembly 100 is intended, in one embodiment, to reside outside a patient while the remainder of catheter assembly 100 is percutaneously introduced into, for example, the cardiovascular system of a patient via a brachial, a radial or a femoral artery. In this embodiment, proximal portion 113 of catheter assembly 100 includes hub 140. Hub 140 includes needle 134 and needle 136, and inflation cannula 128. In one embodiment, relative to the materials for the various cannulas described, a housing of hub 140 is a hard or rigid polymer material, e.g., a polycarbonate or acrylonitrile butadiene styrene (ABS). A distal end of hub 140 has an opening to accommodate a proximal end of catheter body 112. Hub 140 also has a number of cavities at least partially therethrough (extending in a distal to proximal direction) to accommodate needle 134 and needle 136, and inflation cannula 128. A proximal portion of hub 140 flares to separate a spacing between the needles, and inflation cannula 128.

FIG. 1 shows a proximal end of needle 134 and needle 136 each connected (e.g., through an adhesive) to respective injection port 144 and injection port 146. In one embodiment, each injection port includes a luer fitting for conventional syringe attachment. Each injection port allows for the introduction of treatment agent 150, including but not limited to an Apo A-I peptide, a treatment agent including an Apo A-I peptide and/or an ACAT inhibitor. It is appreciated that treatment agent 150 introduced at injection portion 144 and injection port 146 may be the same or different (e.g., a treatment agent including an Apo A-I peptide versus an ACAT inhibitor, a drug, or other cellular component). In this embodiment, inflation cannula 128 terminates at the distal end of balloon inflation port 148.

In one embodiment, catheter assembly 100 also includes or can be configured to include an imaging assembly. Suitable imaging assemblies include ultrasonic imaging assemblies, optical imaging assemblies, such as an optical coherence tomography (OCT) assembly, magnetic resonance imaging (MRI). One embodiment of catheter assembly 100 illustrated in FIG. 1 may include an OCT imaging assembly.

OCT uses short coherent length light (typically with a coherent length of about 10 to 100 microns) to illuminate the object (e.g., blood vessel or blood vessel walls). Light reflected from a region of interest within the object is combined with a coherent reference beam. Interference occurs between the two beams only when the reference beam and reflective beam have traveled the same distance. One suitable OCT setup may be similar to ones disclosed in U.S. Pat. Nos. 5,465,147; 5,459,570; 5,321,501; 5,291,267; 5,365,125; and 5,202,745. A suitable optical assembly for use in conjunction with a catheter assembly is made with fiber optic components that, in one embodiment, can be passed through the guidewire lumen (e.g., guidewire cannula 116 of FIG. 1).

Figure 2:
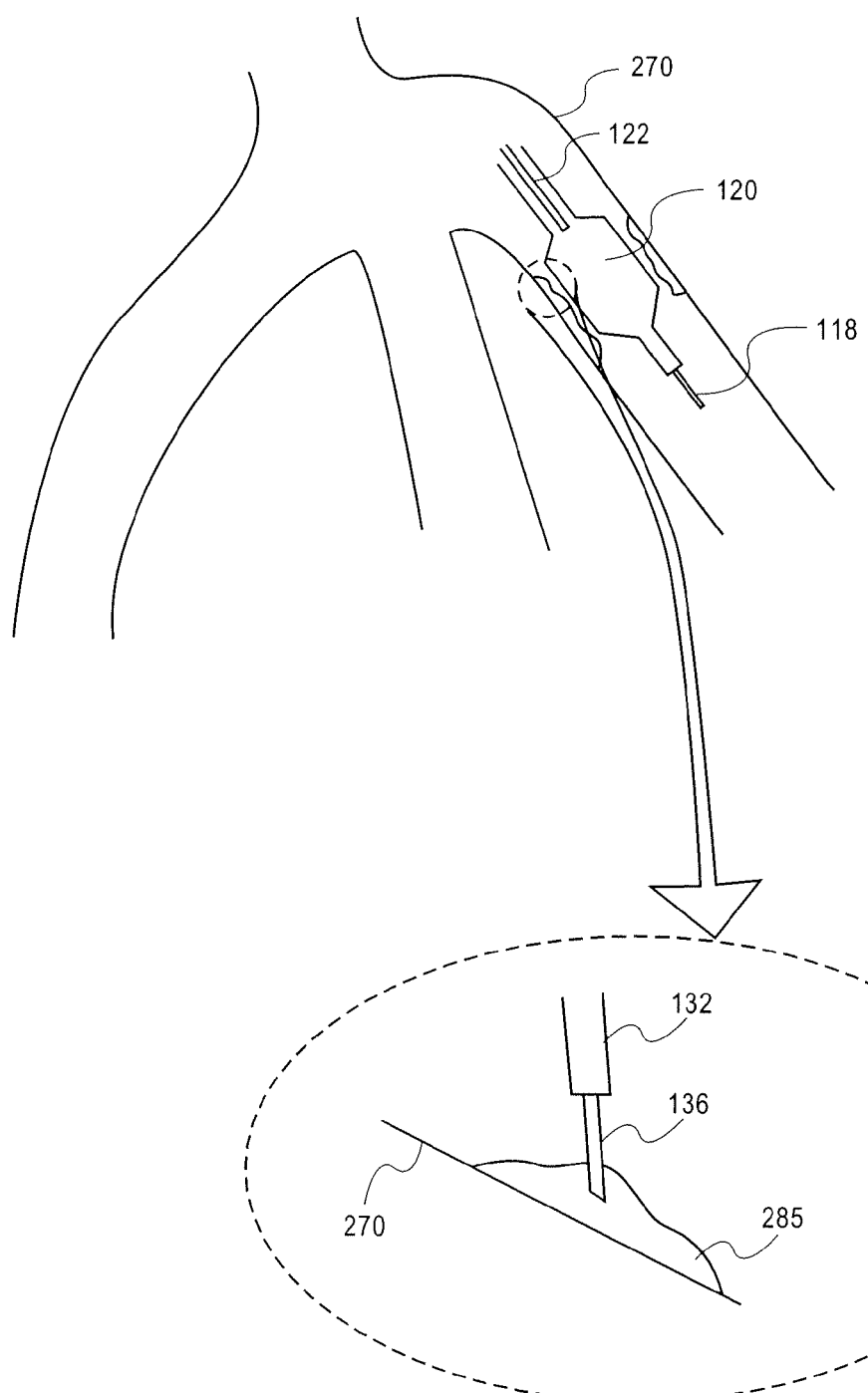
FIG. 2 schematically illustrates a portion of coronary artery network having a catheter assembly introduced therein.
Figure 3:
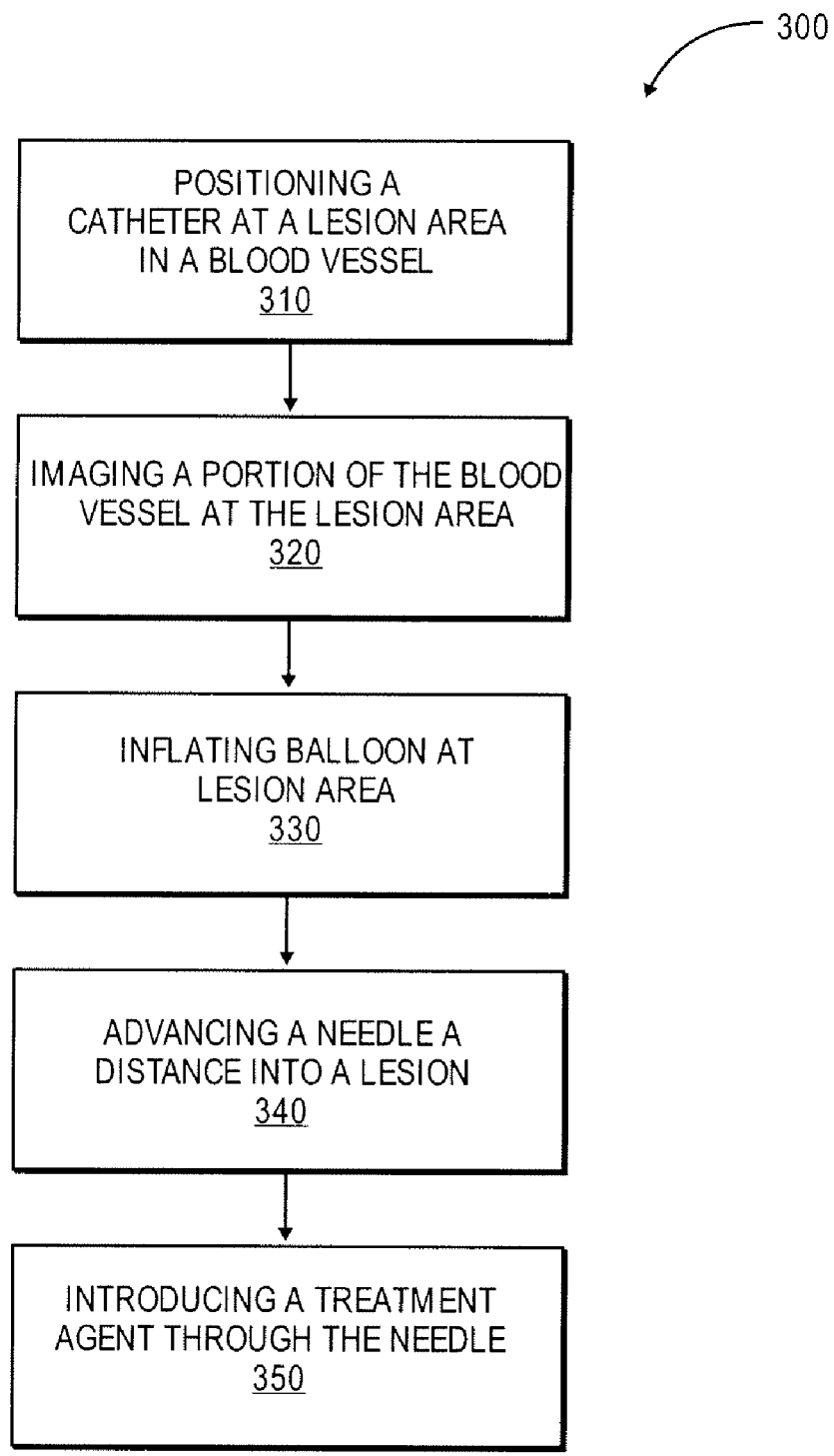
FIG. 3 presents a block diagram for introducing a treatment composition.

The catheter assembly described with reference to FIG. 1 may be used to introduce an Apo A-I peptide, a treatment composition including an Apo A-I peptide and/or an ACAT inhibitor such as described above at a desired location. FIG. 2 illustrates one technique. FIG. 3 presents a block diagram of one technique. With reference to FIGS. 2 and 3 and catheter assembly 100 of FIG. 1, in a one procedure, guidewire 118 is introduced into, for example, an arterial system of a patient (e.g., through the femoral artery) until the distal end of guidewire 118 is upstream of a narrowed lumen of the blood vessel (e.g., upstream of lesion area 285 in vessel 270). Catheter assembly 100 is mounted on the proximal end of guidewire 118 and advanced over the guidewire 118 until catheter assembly 100 is position as desired. In the example shown in FIG. 2, catheter assembly 100 is positioned so that a medial working length of balloon 120 and delivery cannula 130 are at or adjacent the narrowed lumen of vessel 270 (block 310). Imaging techniques may be used to place catheter assembly 100. Once balloon 120 is placed and subject to low inflation pressure, guidewire 118 is removed and replaced in one embodiment with an optical fiber for imaging (e.g., OCT) (block 320).

In this example, vessel 270 is viewed and the lesion area is identified or a thickness of the atherosclerotic lesion is imaged (and possibly measured) (block 320). At this point, balloon 120 is dilated as shown in FIG. 1 by, for example, delivering a fluid to balloon 120 through inflation cannula 128. The inflation of balloon 120 causes delivery cannula 130 to move proximate to or contact the blood vessel wall at the lesion area. Needle 136 is then advanced a distance into the lesion (e.g., atherosclerotic lesion) (block 340). A real time image may be used to advance needle 136. Alternatively, the advancement may be based on a measurement of the blood vessel wall or lesion boundary derived from an optical image. Once in position, an Apo A-I peptide or a treatment composition including an Apo A-I peptide is introduced through needle 136 to the lesion (block 350).

In an embodiment where an ACAT inhibitor is also introduced through catheter assembly 100, an ACAT inhibitor may be introduced through needle 136. In one embodiment, needle 136 may be introduced into a wall of vessel 270 at the lesion area or beyond the vessel (e.g., to a periadventitial space). An ACAT inhibitor may then be introduced through injection port 146.

Figure 4:
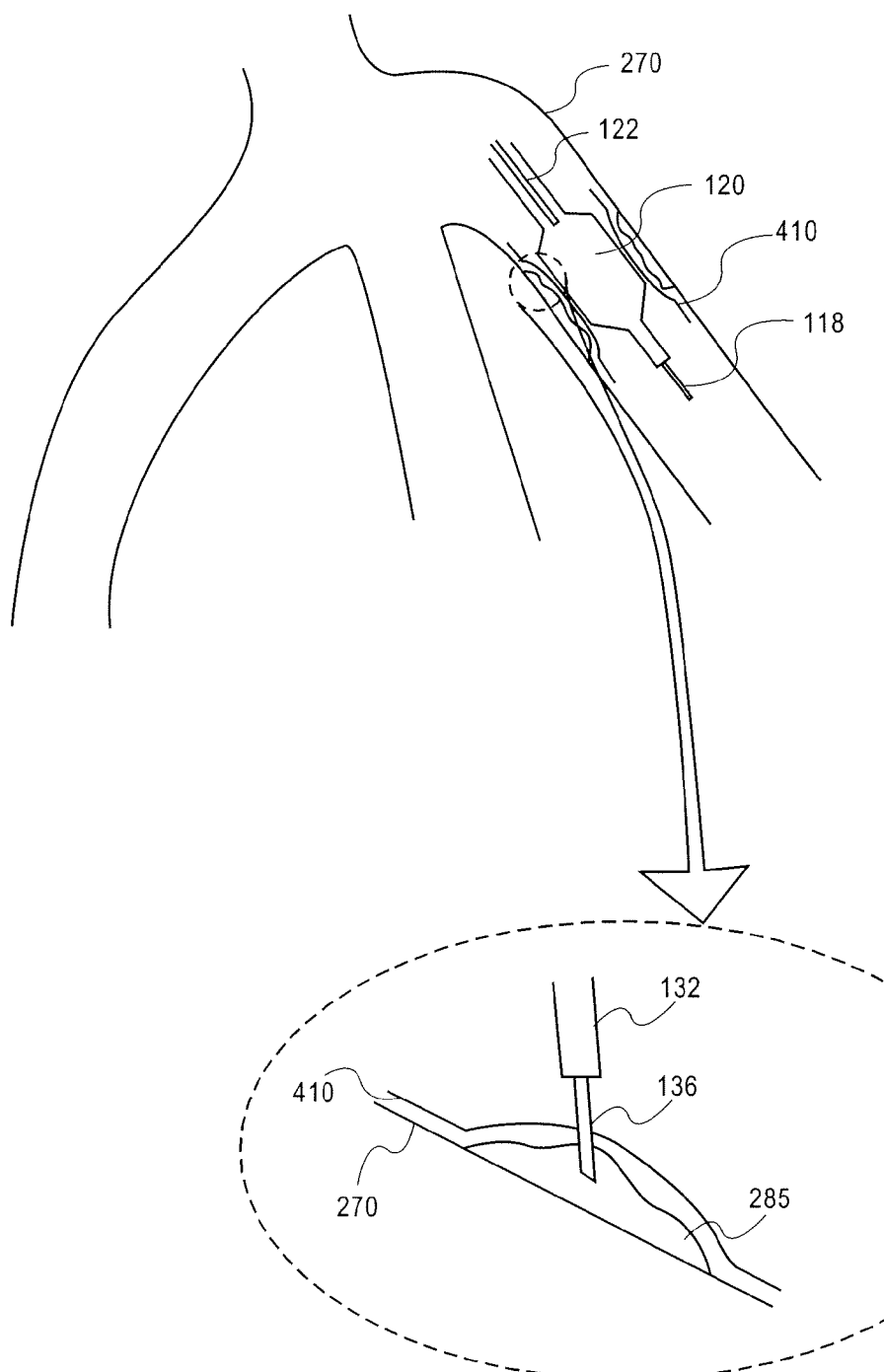
FIG. 4 schematically illustrates a portion of a coronary artery network having a stent placed therein and a catheter assembly introduced therein.

In the above embodiment, an Apo A-I peptide, treatment composition including an Apo A-I peptide, and/or ACAT inhibitor is introduced directly into a blood vessel wall (e.g., a lesion area of a blood vessel wall). Such introduction may follow (either immediately or at some time thereafter) a percutaneous angioplasty (PTCA) by an expanding balloon. Such introduction may also precede or follow the placement of a stent adjacent a lesion area. FIG. 4 shows a coronary blood vessel (e.g., LCX 270) having stent 410 placed adjacent lesion area 285. In one embodiment, stent 410 may be a drug- or other treatment agent-eluting stent. For example, stent 410 may be coated with an ACAT inhibitor to permit a combination therapy of Apo A-I and an ACAT inhibitor. In this embodiment, following a placement of stent 410, needle 136 may be advanced through openings in a cage-like structure of stent 410 into lesion area 285 for delivery of an Apo A-I peptide or a treatment composition including an Apo A-I peptide into lesion area 285.

In the example where stent 410 is a coated stent for eluting an ACAT inhibitor, the stent may be composed of a metal, an alloy, a polymer, or a combination thereof and a treatment agent included in a stent coating or in the body of the stent. Examples of materials used to form stents include, but are not limited to, ELATINITE®, Nitinol (nickel-titanium alloy), stainless steel, tantalum, tantalum-based alloys, platinum, platinum-based alloys, and other metals and their alloys. Alternatively, stent 410 is composed of a bioabsorbable polymer or biostable polymer. A polymer or coating is "bioabsorbable" or "biodegradable" when it is capable of being completely or substantially degraded or eroded when exposed to either an in vivo environment or an in vitro environment having physical, chemical, or biological characteristics substantially similar to those of the in vivo environment within a mammal. A polymer or coating is "degradable or erodible" when it can be gradually broken down, resorbed, absorbed and eliminated by, for example, hydrolysis, enzymolysis, metabolic processes, bulk or surface erosion, and the like within a mammal. It is to be appreciated that traces of residue of polymer may remain following biodegradation. A "biostable" polymer is a polymer that is not bioabsorbable.

Suitable polymers used in embodiments of a material for a body stent 410 (i.e., the structural aspect of the stent as opposed to a coating), include, but are not limited to, hydrophobic, hydrophilic, amphiphilic, biodegradable, or a combination thereof. Examples of hydrophobic polymers include, but are not limited to, poly (ester amide), polystyrene-polyisobutylene-polystyrene block copolymer (SIS), polystyrene, and polyisobutylene. Examples of hydrophilic polymers include, but are not limited to, polymers and co-polymers of hydroxyethyl methacrylate (HEMA); poly (methyl methacrylate) (PMMA); and poly (ethylene glycol) acrylate (PEGA). Examples of biodegradable polymers include, but are not limited to, polymers having repeating units such as, for example, an α-hydroxycarboxylic acid, a cyclic diester of an α-hydroxycarboxylic, a dioxanone, a lactone, a cyclic carbonate, a cyclic oxalate, an epoxide, a glycol, an anhydride, a lactic acid, a glycolic acid, a glycolic acid, a lactide, a glycolide, an ethylene oxide, an ethylene glycol, or combinations thereof. In some embodiments, the biodegradable polymers include, but are not limited, to polyesters, polyhydroxyalkanoates (PHAs), poly (ester amides), amino acids, PEG and/or alcohol groups, polycaprolactones, poly (L-lactide), poly (D,L-lactide, poly (D,L-lactide-co-PEG) block copolymers, poly (D,L-lactide-co-trimethylene carbonate), polyglycolides, poly (lactide-co-glycolide), polydioxanones, polyorthoesters, polyanhydrides, poly (glycolic acid-co-trimethylene carbonate), polyphosphoesters, polyphosphoester urethanes, poly (amino acids), polycyanoacrylates, poly(trimethylene carbonate), poly (imino carbonate), polycarbonates, polyurethanes, co-poly (ether-esters) (e.g., PEO/PLA), polyakylene oxalates, polyphosphazenes, PHA-PEG, and any derivatives, analogs, homologues, salts, copolymers and combinations thereof.

A composition including an ACAT inhibitor may be included in a stent coating on stent 410 or included in the body of stent 410 such as, for example, a biodegradable polymeric stent. The release profile of, for example, ACAT inhibitor and polymer can be controlled by tailoring the chemical composition and crystallinity of the polymer as the coating or the bioabsorbable stent material (e.g., the more crystalline, the slower the release rate).

In the embodiments described with reference to FIGS. 1-4, a catheter assembly for introducing an Apo A-I peptides, a treatment composition including an Apo A-I peptide, and/or an ACAT inhibitor into a wall of a blood vessel (e.g., into a lesion area of the blood vessel) is described. In another embodiment, it may be desired to introduce an Apo A-I peptide, a treatment composition including an Apo A-I peptide and/or an ACAT inhibitor within a blood vessel (i.e., an intra-coronary introduction). Such technique may be used, for example, to deliver an Apo A-I synthetic peptide including an amino acid sequence in an order reverse to an order of an endogenous Apo A-I peptide and/or an Apo A-I peptide that is a chimera of helix 1 and helix 9 of Apo A-I, optionally with an amino acid sequence in reverse order. An intra-coronary introduction of the Apo A-I peptide or a treatment composition including an Apo A-I peptide will promote reverse cholesterol transport from within a lumen of a coronary vessel. Alternatively, an Apo A-I peptide or a treatment composition including an Apo A-I peptide may be introduced regionally, such as injected into an accessible artery through a needle injection.

Figure 5:
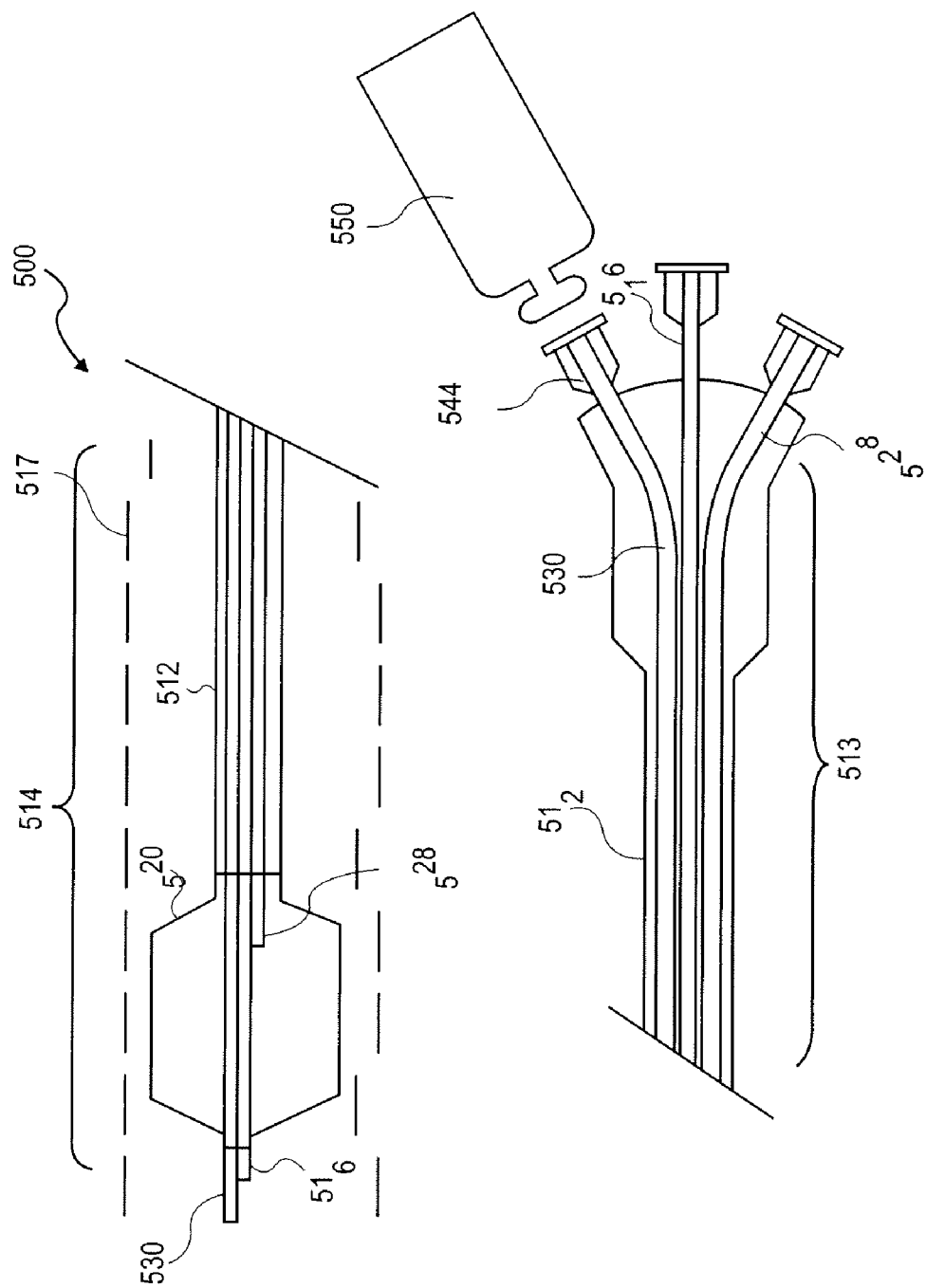
FIG. 5 schematically illustrates a simplified cross-sectional view of a second embodiment of a substance delivery apparatus in the form of a catheter assembly having a balloon and a treatment agent delivery assembly.

FIG. 5 shows blood vessel 517 having catheter assembly 500 disposed therein. Catheter assembly 500 includes proximal portion 513 and distal portion 514. Proximal portion 513 may be external to blood vessel 517 and to the patient. Representatively, catheter assembly 500 may be inserted through a femoral artery and through, for example, a guide catheter and with the aid of a guidewire to a location in the vasculature of a patient. That location may be, for example, a coronary artery. FIG. 5 shows distal portion 514 of catheter assembly 500 positioned at a treatment site within a coronary blood vessel (blood vessel 517).

In one embodiment, catheter assembly 500 includes primary cannula 512 having a length that extends from proximal portion 513 (e.g., located external to a patient during a procedure) to connect to the proximal end or skirt of balloon 520. Primary cannula 512 has a lumen therethrough that includes inflation cannula 528 and delivery cannula 530. Each of the inflation cannula 528 and delivery cannula 530 extend from proximal portion 513 of catheter assembly 500 to distal portion 514. Inflation cannula 528 has a distal end that terminates in balloon 520. Delivery cannula 530 extends through balloon 520 (i.e., beyond a distal end or skirt of balloon 520). In another embodiment, catheter assembly 500 does not include a balloon or inflation cannula.

Catheter assembly 500 also includes guidewire cannula 516 extending, in this embodiment, through balloon 520 to a distal end of catheter assembly 500. Guidewire cannula 516 has a lumen sized to accommodate a guidewire (not shown). Catheter assembly 500 may be an over-the-wire (OTW) configuration where guidewire cannula 516 extends from a proximal end (external to a patient during a procedure) to a distal end of catheter assembly 500. In another embodiment, catheter assembly 500 is a rapid exchange (RX) type catheter assembly where only a portion of catheter assembly 500 (a distal portion including balloon 520) is advanced over the guidewire. FIG. 5 shows an OTW type catheter assembly.

In one embodiment, catheter assembly is introduced into blood vessel 517 in a direction of blood flow, such as through a femoral artery to a location within a coronary artery. Once introduced, balloon 520 is inflated (e.g., with a suitable liquid through inflation cannula 528) to occlude a blood vessel. Following occlusion, an Apo A-I peptide or a treatment composition including an Apo A-I peptide is introduced through delivery cannula 530. FIG. 5 shows treatment agent 550 that may be connected to delivery port 544 and introduced into delivery cannula 530. As noted above, in one embodiment, the delivery of treatment agent 550 will be with the flow of blood through the blood vessel. To retain a treatment agent (e.g., Apo A-I) within a location in a blood vessel for at least a minimum period of time, it may be desirable to inflate a first balloon distal to an injury site (e.g., lesion area) and inflate a second balloon proximal to the injury site, thus isolating the injury site between the two inflated balloons. The distal balloon may be part of catheter assembly 500 (e.g., a dual balloon catheter) or a part of the guidewire (e.g., a PERCU-SURG™ catheter assembly, commercially available from Medtronic, Inc. of Minneapolis, Minn.).

Figure 6:
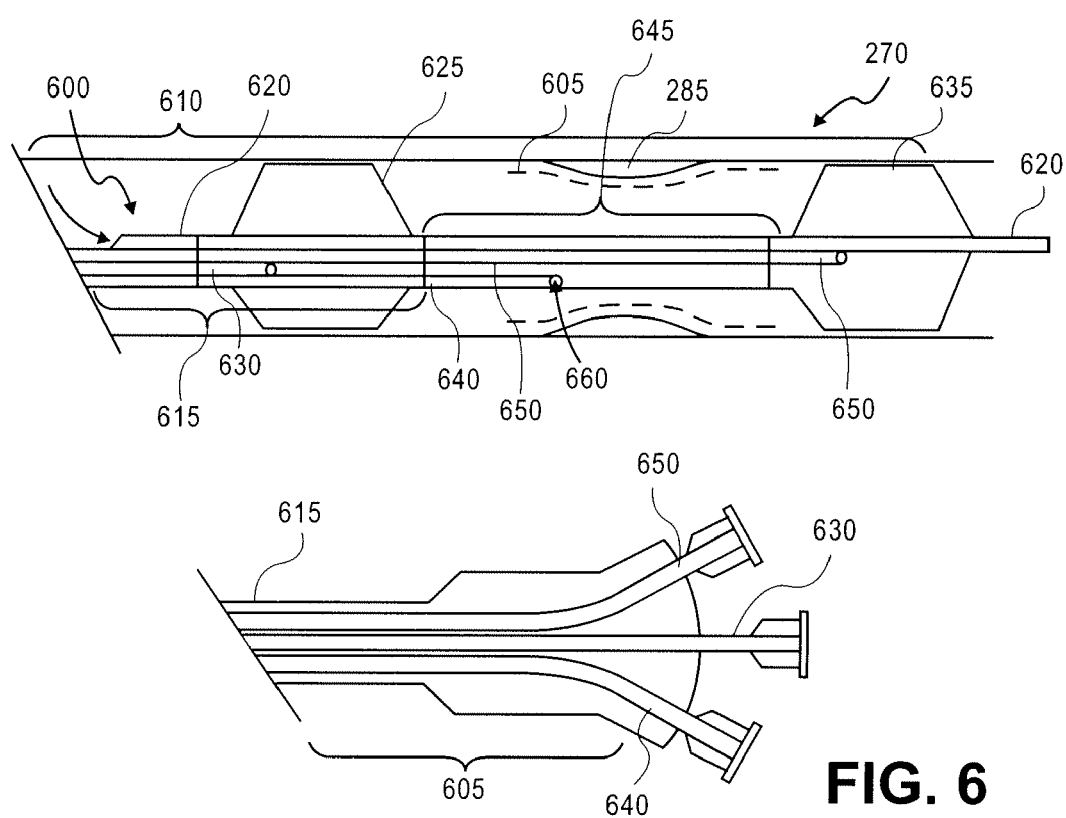
FIG. 6 shows the blood vessel of FIG. 4 and a second embodiment of a catheter assembly to deliver a treatment agent introduced into the blood vessel.

In an effort to improve the target area of an Apo A-I mimetic peptide to a treatment site, such as treatment site 285 in FIG. 2, the treatment site may be isolated prior to delivery. FIG. 6 shows an embodiment of a catheter assembly having two balloons where one balloon is located proximal to treatment site 285 and a second balloon is located distal to treatment site 285. A stent may optionally be placed adjacent to treatment site. FIG. 6 shows stent 605 that may be a drug-eluting stent coated with, for example, an ACAT inhibitor. FIG. 6 shows catheter assembly 600 disposed within blood vessel 100. Catheter assembly 600 has a tandem balloon configuration including proximal balloon 625 and distal balloon 635 aligned in series at a distal portion of the catheter assembly. Catheter assembly 600 also includes primary cannula 615 having a length that extends from a proximal end of catheter assembly 600 (e.g., located external to a patient during a procedure) to connect with a proximal end or skirt of balloon 625. Primary cannula 615 has a lumen therethrough that includes inflation cannula 630 and inflation cannula 650. Inflation cannula 630 extends from a proximal end of catheter assembly 600 to a point within balloon 625. Inflation cannula 630 has a lumen therethrough allowing balloon 625 to be inflated through inflation cannula 630. In this embodiment, balloon 625 is inflated through an inflation lumen separate from the inflation lumen that inflates balloon 635. Inflation cannula 650 has a lumen therethrough allowing fluid to be introduced in the balloon 635 to inflate the balloon. In this manner, balloon 625 and balloon 635 may be separately inflated. Each of inflation cannula 630 and inflation cannula 650 extends from, in one embodiment, the proximal end of catheter assembly 600 through a point within balloon 625 and balloon 635, respectively.

Catheter assembly 600 also includes guidewire cannula 620 extending, in this embodiment, through each of balloon 625 and balloon 635 through a distal end of catheter assembly. Guidewire cannula 620 has a lumen therethrough sized to accommodate a guidewire. No guidewire is shown within guidewire cannula 620. Catheter assembly 600 may be an over the wire (OTW) configuration or a rapid exchange (RX) type catheter assembly. FIG. 6 illustrates an RX type catheter assembly.

Catheter assembly 600 also includes delivery cannula 640. In this embodiment, delivery cannula 640 extends from a proximal end of catheter assembly 600 through a location between balloon 625 and balloon 635. Secondary cannula 645 extends between balloon 625 and balloon 635. A proximal portion or skirt of balloon 635 connects to a distal end of secondary cannula 645. A distal end or skirt of balloon 625 is connected to a proximal end of secondary cannula 645. Delivery cannula 640 terminates at opening 660 through secondary cannula 645. In this manner, a treatment agent such as Apo A-I mimetic peptide may be introduced between balloon 625 and balloon 635 positioned between treatment site 285.

FIG. 6 shows balloon 625 and balloon 635 each inflated to occlude a lumen of blood vessel 100 and isolate treatment site 285. In one embodiment, each of balloon 625 and balloon 635 are inflated to a point sufficient to occlude blood vessel 100 prior to the introduction of a treatment agent. A treatment agent, such as Apo A-I mimetic peptide is then introduced through opening 660.

In the above embodiment, separate balloons having separate inflation lumens are described. It is appreciated, however, that a single inflation lumen may be used to inflate each of balloon 625 and balloon 635. Alternatively, in another embodiment, balloon 635 may be a guidewire balloon configuration such as a PERCUSURG™ catheter assembly where catheter assembly 600 including only balloon 625 is inserted over a guidewire including balloon 635.

Figure 7:
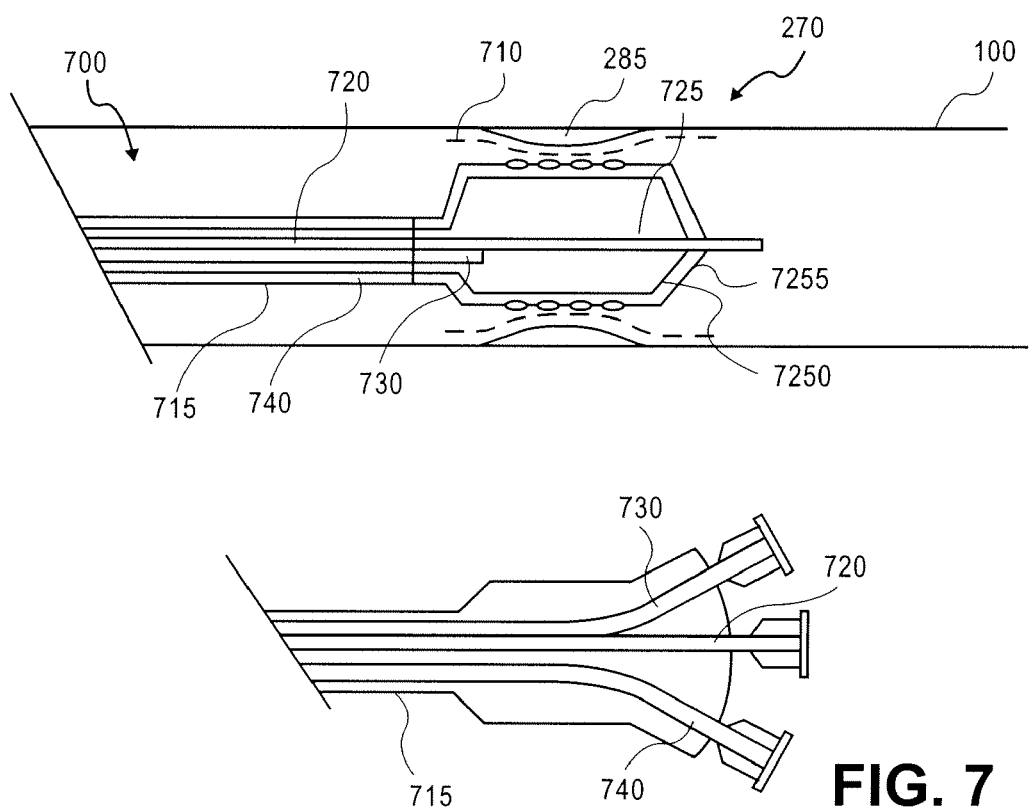
FIG. 7 shows the blood vessel of FIG. 4 and a fourth embodiment of a catheter assembly to delivery a treatment agent introduced into the blood vessel.

FIG. 7 shows another embodiment of a catheter assembly. Catheter assembly 700, in this embodiment, includes a porous balloon through which a treatment agent, such as Apo A-I mimetic peptide, may be introduced. FIG. 7 shows catheter assembly 700 disposed within blood vessel 100. Catheter assembly 700 has a porous balloon configuration positioned at treatment site 285. Catheter assembly 700 includes primary cannula 715 having a length that extends from a proximal end of catheter assembly 700 (e.g., located external to a patient during a procedure) to connect with a proximal end or skirt of balloon 725. Primary cannula 715 has a lumen therethrough that includes inflation cannula 730. Inflation cannula 730 extends from a proximal end of catheter assembly 700 to a point within balloon 725. Inflation cannula 730 has a lumen therethrough allowing balloon 725 to be inflated through inflation cannula 730.

Catheter assembly 700 also includes guidewire cannula 720 extending, in this embodiment, through balloon 725. Guidewire cannula 720 has a lumen therethrough sized to accommodate a guidewire. No guidewire is shown within guidewire cannula 720. Catheter assembly 700 may be an over-the-wire (OTW) configuration or rapid exchange (RX) type catheter assembly. FIG. 7 illustrates an OTW type catheter assembly.

Catheter assembly 700 also includes delivery cannula 740. In this embodiment, delivery cannula 740 extends from a proximal end of catheter assembly 700 to proximal end or skirt of balloon 725. Balloon 725 is a double layer balloon. Balloon 725 includes inner layer 7250 that is a non-porous material, such as PEBAX, Nylon or PET. Balloon 725 also includes outer layer 7255. Outer layer 7255 is a porous material, such as extended polytetrafluoroethylene (ePTFE). In one embodiment, delivery cannula 740 is connected to between inner layer 7250 and outer layer 7255 so that a treatment agent can be introduced between the layers and permeate through pores in balloon 725 into a lumen of blood vessel 100.

As illustrated in FIG. 7, in one embodiment, catheter assembly 700 is inserted into blood vessel 100 so that balloon 725 is aligned with treatment site 285. Blood vessel 100 may include stent 710 disposed adjacent treatment site 285. Following alignment of balloon 725 of catheter assembly 700, balloon 725 may be inflated by introducing an inflation medium (e.g., liquid through inflation cannula 730). In one embodiment, balloon 725 is only partially inflated or has an inflated diameter less than an inner diameter of blood vessel 100 at treatment site 285. In this manner, balloon 725 does not contact or only minimally contacts the blood vessel wall. A suitable expanded diameter of balloon 725 is on the order of 2.0 to 5.0 mm for coronary vessels. It is appreciated that the expanded diameter may be different for peripheral vasculature. Following the expansion of balloon 725, a treatment agent, such as Apo A-I mimetic peptide is introduced into delivery cannula 740. The treatment agent flows through delivery cannula 740 into a volume between inner layer 7250 and outer layer 7255 of balloon 725. At a relatively low pressure (e.g., on the order of two to four atmospheres (atm)), the treatment agent then permeates through the porous of outer layer 7255 into blood vessel 100.

Figure 8:
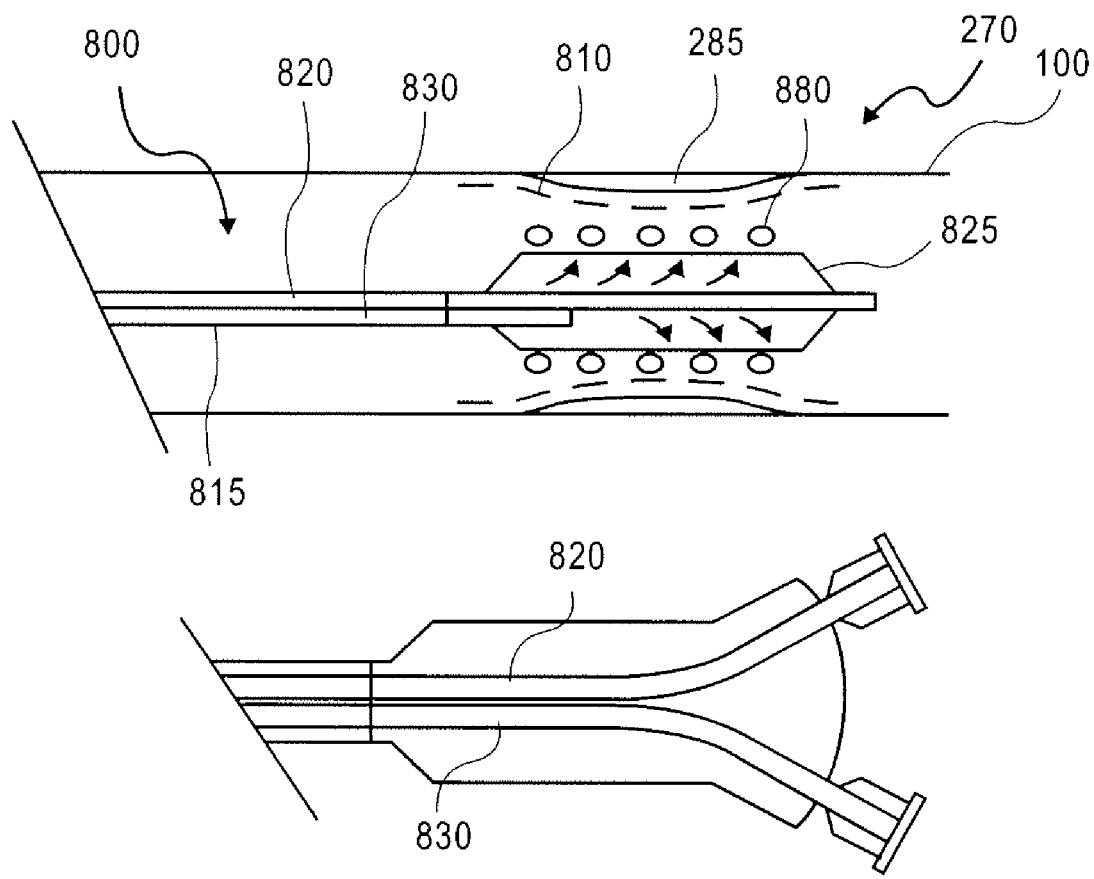
FIG. 8 shows the blood vessel of FIG. 4 and a fifth embodiment of a catheter assembly to deliver a treatment agent introduced into the blood vessel.

FIG. 8 shows another embodiment of a catheter assembly suitable for introducing a treatment agent into a blood vessel. FIG. 8 shows catheter assembly 800 disposed within blood vessel 100. Blood vessel 100 may also include stent 810 disposed adjacent treatment site 285. Catheter assembly 800 includes primary cannula 815 having a length that extends from a proximal end of catheter assembly 800 (e.g., located external to a patient during a procedure) to connect with a proximal and/or skirt of balloon 825. Balloon 825, in this embodiment, is located at a position aligned with treatment site 285 in blood vessel 100.

Disposed within primary cannula 815 is guidewire cannula 820 and inflation cannula 830. Guidewire cannula 820 extends from a proximal end of catheter assembly 800 through balloon 825. A distal end or skirt of balloon 825 is connected to a distal portion of guidewire cannula 820.

Inflation cannula 830 extends from a proximal end of catheter assembly 800 to a point within balloon 825. In one embodiment, balloon 825 is made of a porous material such as ePTFE. A suitable pore size for an ePTFE balloon material is on the order of one μm to 60 μM. The porosity of ePTFE, material can be controlled to accommodate a treatment agent flow rate or particle size by changing a microstructure of an ePTFE tape used to form a balloon, for example, by wrapping around a mandrel. Alternatively, pore size may be controlled by controlling the compaction process of the balloon, or by creating pores (e.g., micropores) using a laser.

ePTFE, as a balloon material is a relatively soft material and tends to be more flexible and conformable with tortuous coronary vessels than conventional balloons. ePTFE also does not need to be folded which will lower its profile and allow for smooth deliverability to distal lesions and the ability to provide therapy to targeted or regional sites post angioplasty and/or stent deployment.

A size of balloon 825 can also vary. A suitable balloon diameter is, for example, in the range of two to five mm. A balloon length may be on the order of eight to 60 mm. A suitable balloon profile range is, for example, approximately 0.030 inches to 0.040 inches.

In one embodiment, a porous balloon may be masked in certain areas along its working length to enable more targeted delivery of a treatment agent. In another embodiment, a sheath may be advanced over a porous balloon (or the balloon withdrawn into a sheath) to allow tailoring of a treatment agent distribution. In another embodiment, a sheath may have a window for targeting delivery of the treatment agent through a porous balloon. In another embodiment, a liner inside a porous balloon may be used to target preferential treatment agent delivery. For example, the liner may have a window through which a treatment agent is delivered, e.g., on one side of a liner for delivery to one side of a vessel wall. This type of configuration may be used to address eccentric lesions.

In an alternative embodiment, rather than using a porous material like ePTFE for forming a porous balloon (e.g., balloon 825 in FIG. 8), a conventional balloon material such as PEBAX, Nylon or PET may be used that has tens or hundreds of micropores around its circumference for treatment agent diffusion. A suitable pore size may range, for example, from approximately five to 100 microns. Pores may be created by mechanical means or by laser perforation. Pore distribution along a balloon surface may be inhomogeneous to tailor distribution of treatment agent delivery.

According to any of the embodiments described with reference to FIG. 8 and the accompanying text, a treatment agent such as Apo A-I mimetic peptide may be introduced through the inflation cannula (e.g., inflation cannula 830) to expand the balloon (e.g., balloon 825). In the example of a balloon of a porous material, such as balloon 825, the treatment agent will expand balloon 825 and at relatively low pressure (e.g., 2-4 atm) diffuse through pores in the porous balloon material to treatment site 280 within a lumen of blood vessel 100. FIG. 8 shows treatment agent 880 diffusing through balloon 825 into a lumen of blood vessel 100. Since balloon 825 is positioned at treatment site 285, treatment agent 880 is diffused at or adjacent (e.g., proximal or distal) to treatment site 285.

The above techniques relate generally to the delivery of a treatment agent such as Apo A-I mimetic peptide through a percutaneous method into a blood vessel or beyond a blood vessel. Other techniques for delivering a treatment agent include direct injection into the pericardium or laparoscopic introduction such as used in bypass surgery or valve repair to a target in the periadventia or myocardium. Surgical delivery techniques are also suitable and include subxiphoid, periadvential (e.g., at the time of a coronary artery bypass graft procedure) or other procedure.

In the preceding detailed description, reference is made to specific embodiments thereof. It will, however, be evident that various modifications and changes may be made thereto without departing from the broader spirit and scope of the following claims. The specification and drawings are, accordingly, to be regarded in an illustrative rather than a restrictive sense.

What is claimed is:

1. A method comprising:
locally introducing a composition comprising a carrier and an apolipoprotein A-I (Apo A-I) synthetic mimetic peptide at a particular coronary region wherein the peptide has a property that renders the peptide effective in reverse cholesterol transport and is selected from the group consisting of:
  (i) An 18 amino acid peptide, DWFKAFYDKVAEK-FKEAF (SEQ ID NO: 1);
  (ii) An 18 amino acid peptide, DWLKAFYDKVAEK-LKEAF (SEQ ID NO: 2);
  (iii) A 33 amino acid peptide, PALEDLRQGLLPVLES-FKVFLSALEEYTKKLNTQ (SEQ ID NO: 3);
  (iv) Ac-DWFKAFYDKVAEKFKEAF-$NH_2$ (SEQ ID NO: 4);
  (v) Ac-PALEDLRQGLLPVLESFKVFLSALEEYTKK-LNTQ-$NH_2$ (SEQ ID NO: 5);
  (vi) Ac-FAEKFKEAVKDYFAKFWD-$NH_2$ (SEQ ID NO: 6);
  (vii) Ac-FAEKLKEAVKDYFAKLWD-$NH_2$ (SEQ ID NO: 7);
  (viii) Ac-NLKKTYEELASLFSVKFSELVPLLGQRL-DELAP-$NH_2$ (SEQ ID NO: 8);
  (ix) Ac-LKLLDNWDSVTSTFSKLREQLGPALEDL-RQGLL-$NH_2$ (SEQ ID NO: 9); and
  (x) Ac-PALEDLRQGLLPKLLDNWDSVTSTFSKL-REQLG-$NH_2$ (SEQ ID NO: 10).

2. The method of claim 1 wherein the particular coronary region comprises a particular region in a coronary blood vessel, the method further comprising:
advancing a delivery device through a lumen of the coronary blood vessel to the particular region in the coronary blood vessel; and
introducing the composition through the delivery device.

3. The method of claim 2, further comprising, after advancing the delivery device, isolating the particular region in the coronary blood vessel by inflating at least two inflatable member components of the delivery device.

4. The method of claim 2 wherein introducing comprises injecting the composition into the particular region via a needle attached to the delivery device.

5. The method of claim 2 wherein the particular region of the coronary blood vessel comprises one of a stenotic region, a pericardial sack, or a periadvential space.

6. The method of claim 2 wherein the delivery device comprises a balloon catheter, the balloon catheter selected from the group consisting of a porous balloon catheter device or a dual-balloon catheter device.

7. The method of claim 1 wherein the carrier is selected from the group consisting of a liposome, a polymersome, a micelle, a particle, a gel, and a microbubble.

8. The method of claim 7 wherein the particle is one of a microparticle, a nanoparticle, a core-shell particle, a microrod, or a nanorod.

9. The method of claim 1 wherein the carrier comprises one of a precipitated peptide particle, a porous glass particle, and a rod.

10. The method of claim 1, further comprising, co-administering one of cholesterol esterase, PEA-TEMPO, poly(L-arginine), or Acyl CoA cholesterol:acyltransferase to the particular coronary region.

11. The method of claim 1, further comprising, simultaneously administering one of cholesterol esterase, PEA-TEMPO, poly(L-arginine), or Acyl CoA cholesterol:acyltransferase to the particular coronary region.

* * * * *

SEQUENCE LISTING

```
<160> NUMBER OF SEQ ID NOS: 12

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Trp Phe Lys Ala Phe Tyr Asp Lys Val Ala Glu Lys Phe Lys Glu
  1               5                  10                  15

Ala Phe

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Trp Leu Lys Ala Phe Tyr Asp Lys Val Ala Glu Lys Leu Lys Glu
  1               5                  10                  15

Ala Phe

<210> SEQ ID NO 3
<211> LENGTH: 34
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 3

Pro Ala Leu Glu Asp Leu Arg Gln Gly Leu Leu Pro Val Leu Glu Ser
  1               5                  10                  15

Phe Lys Val Phe Leu Ser Ala Leu Glu Glu Tyr Thr Lys Lys Leu Asn
             20                  25                  30

Thr Gln

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: n-term acetylated
<220> FEATURE:
<223> OTHER INFORMATION: c-term amidated

<400> SEQUENCE: 4

Asp Trp Phe Lys Ala Phe Tyr Asp Lys Val Ala Glu Lys Phe Lys Glu
  1               5                  10                  15

Ala Phe

<210> SEQ ID NO 5
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: n-term acetylated
<220> FEATURE:
<223> OTHER INFORMATION: c-term amidated

<400> SEQUENCE: 5

Pro Ala Leu Glu Asp Leu Arg Gln Gly Leu Leu Pro Val Leu Glu Ser
  1               5                  10                  15

Phe Lys Val Phe Leu Ser Ala Leu Glu Glu Tyr Thr Lys Lys Leu Asn
             20                  25                  30

Thr Gln

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: n-term acetylated
<220> FEATURE:
<223> OTHER INFORMATION: c-term amidated

<400> SEQUENCE: 6

Phe Ala Glu Lys Phe Lys Glu Ala Val Lys Asp Tyr Phe Ala Lys Phe
  1               5                  10                  15

Trp Asp

<210> SEQ ID NO 7
<211> LENGTH: 18
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: n-term acetylated
<220> FEATURE:
<223> OTHER INFORMATION: c-term amidated

<400> SEQUENCE: 7

Phe Ala Glu Lys Leu Lys Glu Ala Val Lys Asp Tyr Phe Ala Lys Leu
 1               5                  10                  15

Trp Asp

<210> SEQ ID NO 8
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: n-term acetylated
<220> FEATURE:
<223> OTHER INFORMATION: c-term amidated

<400> SEQUENCE: 8

Asn Leu Lys Lys Thr Tyr Glu Glu Leu Ala Ser Leu Phe Ser Val Lys
 1               5                  10                  15

Phe Ser Glu Leu Val Pro Leu Leu Gly Gln Arg Leu Asp Glu Leu Ala
                20                  25                  30

Pro

<210> SEQ ID NO 9
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: n-term acetylated
<220> FEATURE:
<223> OTHER INFORMATION: c-term amidated

<400> SEQUENCE: 9

Leu Lys Leu Leu Asp Asn Trp Asp Ser Val Thr Ser Thr Phe Ser Lys
 1               5                  10                  15

Leu Arg Glu Gln Leu Gly Pro Ala Leu Glu Asp Leu Arg Gln Gly Leu
                20                  25                  30

Leu

<210> SEQ ID NO 10
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: n-term acetylated
<220> FEATURE:
<223> OTHER INFORMATION: c-term amidated

<400> SEQUENCE: 10

Pro Ala Leu Glu Asp Leu Arg Gln Gly Leu Leu Pro Lys Leu Leu Asp
 1               5                  10                  15

Asn Trp Asp Ser Val Thr Ser Thr Phe Ser Lys Leu Arg Glu Gln Leu
```

```
                        20                  25                  30
Gly

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Arg Pro Pro Arg
 1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Pro Pro Pro
 1
```